US011535895B2

(12) United States Patent
Jiang

(10) Patent No.: US 11,535,895 B2
(45) Date of Patent: Dec. 27, 2022

(54) METHODS OF DETECTING LUNG CANCER

(71) Applicants: UNIVERSITY OF MARYLAND, BALTIMORE, Baltimore, MD (US); THE UNITED STATES GOVERNMENT AS REPRESENTED BY THE DEPARTMENT OF VETERANS AFFAIRS, Washington, D.C., DC (US)

(72) Inventor: Feng Jiang, Ellicott City, MD (US)

(73) Assignees: UNIVERSITY OF MARYLAND, BALTIMORE, Baltimore, MD (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 267 days.

(21) Appl. No.: 16/603,061

(22) PCT Filed: Apr. 5, 2018

(86) PCT No.: PCT/US2018/026329
§ 371 (c)(1),
(2) Date: Oct. 4, 2019

(87) PCT Pub. No.: WO2018/187624
PCT Pub. Date: Oct. 11, 2018

(65) Prior Publication Data
US 2021/0108269 A1    Apr. 15, 2021

Related U.S. Application Data

(60) Provisional application No. 62/482,222, filed on Apr. 6, 2017.

(51) Int. Cl.
*C12Q 1/6886* (2018.01)
*C12Q 1/686* (2018.01)

(52) U.S. Cl.
CPC .......... *C12Q 1/6886* (2013.01); *C12Q 1/686* (2013.01); *C12Q 2525/207* (2013.01); *C12Q 2561/113* (2013.01); *C12Q 2600/178* (2013.01)

(58) Field of Classification Search
None
See application file for complete search history.

(56) References Cited

U.S. PATENT DOCUMENTS

| 2010/0070191 A1 | 3/2010 | Gold |
| 2012/0157336 A1 | 6/2012 | Keller |
| 2012/0225925 A1 | 9/2012 | Sozzi |
| 2015/0072890 A1 | 3/2015 | James |
| 2015/0191794 A1* | 7/2015 | Sozzi ................ C12Q 1/6886 514/789 |
| 2015/0197812 A1* | 7/2015 | Burwinkel .......... C12Q 1/6886 506/9 |
| 2019/0131016 A1* | 5/2019 | Cohen .................... G16H 50/30 |

FOREIGN PATENT DOCUMENTS

| WO | 2011025919 A1 | 3/2011 |
| WO | 2016038119 A1 | 3/2016 |
| WO | 2016187404 A1 | 11/2016 |

OTHER PUBLICATIONS

Bishop et al. Accurate Classification of Non-Small Cell Lung Carcinoma Using a Novel MicroRNA-Based Approach. Clin. Cancer Res 16(2):610-619. (Year: 2010).*
Miotto et al. Quantification of Circulating miRNAs by Droplet Digital PCR: Comparison of EvaGreen- and TaqMan-Based Chemistries. Cancer Epidemiol Biomarkers Prev 23(12):2638-42. (Year: 2014).*
Li et al. Non-small cell lung cancer associated microRNA expression signature: integrated bioinformatics analysis, validation and clinical significance. Oncotarget 8(15): 24564-24578. (Year: 2017).*
International Search Report from Appl. No. EP18780446, dated Dec. 23, 2020.
Tomasetti et al., Circulating epigenetic biomarkers in lung malignancies: from early diagnosis to therapy, lung cancer; (2016), 107:65-72.
Jun Shen et al., Analysis of microRNAs in Sputum to Improve Computed Tomography for Lung Cancer Diagnosis, Journal of Thoracic Oncology, (2014), 9:33-40.
Xianfeng Li et al., combining serum miRNAs, CEA, and CYFRA21-1 with imaging and clinical features to distinguish benign and malignant pulmonary nodules; A pilot study, World Journal of Surgical Oncology, (2017), 15:CP55762511.
International Search Report from Appl. No. PCT/US18/26329, dated Aug. 7, 2018.

* cited by examiner

*Primary Examiner* — Samuel C Woolwine
(74) *Attorney, Agent, or Firm* — Nevrivy Patent Law Group P.L.L.C.

(57) ABSTRACT

The present invention provides a method of predicting whether a pulmonary nodule in a subject is benign or non-small cell lung cancer, comprising obtaining the results of an assay that measures an expression level of miR205-5p in a plasma sample from the subject; obtaining the results of an assay that measures an expression level of miR126 in a plasma sample from the subject; obtaining the results of an assay that provides a size of the pulmonary nodule in the subject; and calculating a probability value based on the combination of the expression levels of miR205-5p and miR126, and the size of the pulmonary nodule, wherein if the probability value exceeds a specified threshold, the pulmonary nodule is predicted as non-small cell lung cancer.

15 Claims, 8 Drawing Sheets

Specification includes a Sequence Listing.

FIG. 8

| miRNAs | Mean (SD) in patients with benign PNs | Mean (SD) in patients with malignant PNs | P |
|---|---|---|---|
| miR-21-5p | 9.6745 (4.669) | 20.9623 (23.7658) | 0.0398 |
| miR-103a-3p | 1.9925 (1.8432) | 7.9557 (11.3437) | 0.0278 |
| miR-126-3p | 3.6523 (2.8326) | 22.1716 (27.8393) | 0.0437 |
| miR-135a-5p | 0.0326 (0.0279) | 0.0104 (0.0113) | 0.0053 |
| miR-145-5p | 1.3283 (0.9871) | 0.6889 (1.2462) | 0.0032 |
| miR-141-3p | 0.0398 (0.0486) | 0.0587 (0.1278) | 0.0380 |
| miR-193b-3p | 0.0448 (0.0488) | 0.0689 (0.0232) | 0.0150 |
| miR-200b-3p | 0.0289 (0.0368) | 0.0098 (0.0089) | 0.0020 |
| miR-205-5p | 0.0237 (0.0210) | 0.0785 (0.1127) | 0.0030 |
| miR-210 | 0.4576 (0.6036) | 0.9095 (0.9865) | 0.0073 |
| miR-301b | 0.1857 (0.1898) | 0.8965 (1.0367) | 0.0100 |

SEQUENCE LISTING

<160> NUMBER OF SEQ ID NOS: 12

<210> SEQ ID NO 1
<211> LENGTH: 85
<212> TYPE: DNA
<213> ORGANISM: Homo sapiens

<400> SEQUENCE: 1
cgctggcgac gggacattat tacttttggt acgcgctgtg acacttcaaa ctcgtaccgt      60
gagtaataat gcgccgtcca cggca                                           85

<210> SEQ ID NO 2
<211> LENGTH: 110
<212> TYPE: DNA
<213> ORGANISM: Homo sapiens

<400> SEQUENCE: 2
aaagatcctc agacaatcca tgtgcttctc ttgtccttca ttccaccgga gtctgtctca      60
tacccaacca gatttcagtg gagtgaagtt caggaggcat ggagctgaca                110

<210> SEQ ID NO 3
<211> LENGTH: 110
<212> TYPE: DNA
<213> ORGANISM: Homo sapiens

<400> SEQUENCE: 3
acccggcagt gcctccaggc gcagggcagc ccctgcccac cgcacactgc gctgccccag      60
acccactgtg cgtgtgacag cggctgatct gtgcctgggc agcgcgaccc                110

<210> SEQ ID NO 4
<211> LENGTH: 5179
<212> TYPE: DNA
<213> ORGANISM: Homo sapiens

<400> SEQUENCE: 4
tttcagttgg aaggaggtag ggaaaataag tgctttaatt cctaggkattt tggaagtaaa      60 aatggaacac cagacaaaaa tggaattttt aggcaaatgt aaagctttgt acttgggtat     120
ctcaaagtat tatacagtgt aaactatcat gattattaac caactagaag tagttctttt     180
ttttaaattt tatttttaat tttagacatg agggtcttgc tatgttgccc aggctgaagt     240
ggctactgac aggcacgatg tggcactgca gcctggaact cttgggctta agtgatcctt     300
cctgcttctt ctatcttaaa aaaaaaagt tacgcttgct tgttaaaata ttttttaaaat     360 gctgtgttta aactaagaag taaatatcca ccccacctct gacttctaaa aattatctaa     420
agtatgactg gtaagatttt tacctttaat cccacataag tctaaaattt gtgttcattt     480
ccaacaacca aagtgtgtca cttttatacc agaattttgt cctgcttata cgtttagtac     540
agaaatctca tgggagagag catccatgca tttacaaatt gttattgaat tattttattg     600
aatgatgaca cccaaactga gctagaacat aattctggct ctgctagtac atcttctgtg     660
tgatcttgga caagtcactc tactttcctt tcaattttct tttctcacag ggagataatc     720
ataaaaacga ctgtaaagta cagcacttca tagagtgctt tttgtttaaa gagctgacaa     780
taaatacgag tctcaaggtc taggaaagcc tccctcacaa cctgagctgc ttaggacaa      840 gggattttct tttgaatcag cagtaccttta tttgtgtatc tgtgatagag ttcctggtac     900
ataagaaggt ctcaataaat atgtgaattt atgaatatta ggcagattgc aaccttgaca     960
ggccactgcc tcttaaatct cctttctgtg atctttaat atttaacatc taaaaggccg    1020

```
ccgctacttg ctttgggata agtatccccg gtatgtactt taaaatgccc aagcctagag   1080
aaatgattct tgtcttaagg gcaccatttc gctctcccac cgtaaagcgc cccaggcttg   1140
ggatctgggt cccaaggcta cagggaagag tttggaacgg gaagctcatc ttccggccct   1200
ctgattggcc ggctcgcact ccactcacgc ggcgcgcagc tctgattggc ctcggcggca   1260
cccctcgtcc cgcgactact tgtgtgctg gggcggcgcg ctccggtcct cccgctcagc    1320
tggcggtctg ggctgctctg gggcagccct tcggtccact gctctgcatc gcgggcgccg   1380
ggaattttcc gagtccgagc gggttgctgc ttttgctcag aggacatcca tgaccctaat   1440 ggtcttttg ttcaagataa agtgattttt tgcctttgtt gattaactgg acaaattcag     1500
catgtagagc gcatgaagta caggacaata aagcttccta cacatatcac caggaggatc   1560
tctttgaaag attcactgca ggactaccag agagaataat ttgtctgaag catcatgtgt   1620
tgaaacaaca gaagtctatt cacctgtgca ctaactagaa acagagttac aatgttttca   1680
attctttgag ctccaggact ccagggaagt gagttgaaaa tctgaaaatg cggccatgga   1740
ctggttcctg gcgttggatt atgctcattc ttttgcctg ggggaccttg ctgttttata    1800
taggtggtca cttggtacga gataatgacc atcctgatca ctctagccga gaactgtcca   1860
agattctggc aaagcttgaa cgcttaaaac aacagaatga agacttgagg cgaatggccg   1920
aatctctccg gataccagaa ggccctattg atcaggggcc agctatagga agagtacgcg   1980
ttttagaaga gcagcttgtt aaggccaaag aacagattga aaattacaag aaacagacca   2040
gaaatggtct ggggaaggat catgaaatcc tgaggaggag gattgaaaat ggagctaaag   2100
agctctggtt tttcctacag agtgaattga agaaattaaa gaacttagaa ggaaatgaac   2160
tccaaagaca tgcagatgaa tttcttttgg atttaggaca tcatgaaagg tctataatga   2220
cggatctata ctacctcagt cagacagatg gagcaggtga ttggcgggaa aaagaggcca   2280
aagatctgac agaactggtt cagcggagaa taacatatct tcagaatccc aaggactgca   2340
gcaaagccaa aaagctggtg tgtaatatca acaaaggctg tggctatggc tgtcagctcc   2400
atcatgtggt ctactgcttc atgattgcat atggcaccca gcgaacactc atcttggaat   2460
ctcagaattg gcgctatgct actggtggat gggagactgt atttaggcct gtaagtgaga   2520
catgcacaga cagatctggc atctccactg gacactggtc aggtgaagtg aaggacaaaa   2580
atgttcaagt ggtcgagctt cccattgtag acagtcttca tccccgtcct ccatatttac   2640
ccttggctgt accagaagac ctcgcagatc gacttgtacg agtgcatggt gaccctgcag   2700
tgtggtgggt gtctcagttt gtcaaatact tgatccgccc acagccttgg ctagaaaaag   2760
aaatagaaga agccaccaag aagcttggct tcaaacatcc agttattgga gtccatgtca   2820
gacgcacaga caaagtggga acagaagctg ccttccatcc cattgaagag tacatggtgc   2880
atgttgaaga acattttcag cttcttgcac gcagaatgca agtggacaaa aaaagagtgt   2940
atttggccac agatgaccct tctttattaa aggaggcaaa aacaaagtac cccaattatg   3000
aatttattag tgataactct atttcctggt cagctggact gcacaatcga tacacagaaa   3060
attcacttcg tggagtgatc ctggatatac attttctctc tcaggcagac ttcctagtgt   3120
gtactttttc atcccaggtc tgtcgagttg cttatgaaat tatgcaaaca ctacatcctg   3180
atgcctctgc aaacttccat tctttagatg acatctacta ttttgggggc cagaatgccc   3240
acaatcaaat tgccatttat gctcaccaac cccgaactgc agatgaaatt cccatggaac   3300
ctggagatat cattggtgtg gctggaaatc attgggatgg ctattctaaa ggtgtcaaca   3360
```

```
ggaaattggg aaggacgggc ctatatccct cctacaaagt tcgagagaag atagaaacgg    3420
tcaagtaccc cacatatcct gaggctgaga aataaagctc agatggaaga gataaacgac    3480
caaactcagt tcgaccaaac tcagttcaaa ccatttcagc caaactgtag atgaagaggg    3540
ctctgatcta acaaaataag gttatatgag tagatactct cagcaccaag agcagctggg    3600
aactgacata ggcttcaatt ggtggaattc ctctttaaca agggctgcaa tgccctcata    3660
cccatgcaca gtacaataat gtactcacat ataacatgca aacaggttgt tttctacttt    3720 gccccttttca gtatgtcccc ataagacaaa cactgccata ttgtgtaatt taagtgacac    3780
agacattttg tgtgagactt aaaacatggt gcctatatct gagagacctg tgtgaactat    3840
tgagaagatc ggaacagctc cttactctga ggaagttgat tcttatttga tggtggtatt    3900
gtgaccactg aattcactcc agtcaacaga ttcagaatga gaatggacgt ttggtttttt    3960
tttgtttttg tttttgtttt ttcctttata aggttgtctg ttttttttttt tttaaataat    4020 tgcatcagtt cattgacctc atcattaata agtgaagaat acatcagaaa ataaatatt    4080 cactctccat tagaaaattt tgtaaaacaa tgccatgaac aaattcttta gtactcaatg    4140
tttctggaca ttctctttga taacaaaaaa taaattttaa aaaggaattt tgtaaagttt    4200
ctagaatttt atatcattgg atgatatgtt gatcagcctt atgtgaaga actgtgataa    4260 aaagaggagc ttttagttt ttcagcttat ttactttgtt tttttttcctg tttctgatat    4320 agtaactaat tcttaactca gagacattgg tccattttaa tactgaaaac caattttcat    4380
tggtacacat tacaaaattg ctaagaacac tgtttgggag ctttcattct catattttgg    4440
acattgtttt aattgagtga ataatcata actccttgct cccagagaag ctatcacctc    4500
catttctaaa accatttcag gtttgtttgg tagtctttct taatgtattt attatcgctt    4560
tttgtgagta gggtcctgtt ttatccagga accaatttct gccctagcct atcatgccct    4620
gcttttgaga gtaccaggta tctttgggat tgggaagctg gctgtttcag aagtatatgt    4680
ctcatagtgt gcagaacttg gtgaccaagt gagaagcggg accaatggga gactcacaat    4740
ggactgagtc ttgggattat cttttccaaa ttcttccatg ttagaatcac ttcagaaaat    4800
aagactttga tgctttgtct ctgagcatca ttttctcct cataaaaaca cttccttatt    4860
gtatgtagcc tgcctcctac agaggcctgg taggtgttac tgcattctaa aagaaaaatg    4920
tcatctctgt aggagcgact atcaggccta gtgtgaaata ttagggatcc taggcagaag    4980
agctattagt cctggccttc atatcttcac caaatgaaaa tactgtatat aaaatttcac    5040
caccaaactt aactaaattc ttttttctcaa gtcaagcctc ccaaagaaaa aagaaattaa    5100
cttcctacag tgtcagcaag caattttcca tttagttttg gtacaaataa aagtcatttg    5160
aaacaaaaaa aaaaaaaaa                                                 5179
```

<210> SEQ ID NO 5
<211> LENGTH: 1134
<212> TYPE: DNA
<213> ORGANISM: Homo sapiens

<400> SEQUENCE: 5

```
gttctcattt ttctactgct cgtggattta cgcgcacgtt ggaaccgaag agagctctgt      60
tgttgcaatg ttcagcccac aagagcttac tggtgaagga atgggacaag acccatcttt     120
atgcaaagcc agcgttacag taatgttcca gcatctcata atctatcctg gggaattcag     180
ctgcctccca gggtgaatac aggtattcct gatgacagtc tgcctctatc ttacagagca     240
gcttgttgct atataccatt gaaaagcctt cagagctgag aggtactact aaccaataac     300
```

```
ctgcttggct caaagggcca gcaccttctc tctaaagccc aagaggagtt tgaggaaaac    360
taggtgtctg tgttcactcc aggctgaagt tacaggtctg agcaaataag gtgtataaaa    420
aatggaatct gtcttggagg acatcagaag gtgaattttc aagttcttg acaacctag      480 ctgttgaaaa gctttctggg tttgggggt atttcagatg taccttaaag tgttagcaga    540
cacagattaa gacactggga gccaatgaaa cagcagttga gggtttgctg tgtatcacat    600
ttctgtattt tatcaccccc ttcctgcaac attatttatc tggaatctac ctgccctttt    660
gttttttaga tacaagggct tggttttgtt acccaggctg gtttcaaggc catagcttta    720
agagatcctc tcaccacaga tttccaaagt gctgggattg caggtgtgat tcatggcacc    780
cagactttgc tgcctttctt acatgatcca ggcccagaac ccaaactcag gcactgtata    840
gatgaccact ttcgtaaact actgacctag cttgttgcca attgttgatt gaacttccca    900
taactccact tcgtgtctgt tcctctgtat acagccacct tctgttcccg tcatgagcct    960
ttaggtctcc atttgcatat tgcaaatact atgttccatg taggtagctc attcagggcc   1020
ttgctcttca cttcaaaaaa ggttcccttg aggactggct gtcaatttgt gttgctgtgt   1080
tggttgttga tgaaaataat aaaatgattg attacataaa aaaaaaaaaa aaaa         1134
```

<210> SEQ ID NO 6
<211> LENGTH: 22
<212> TYPE: DNA
<213> ORGANISM: artificial sequence
<220> FEATURE:
<223> OTHER INFORMATION: primer

<400> SEQUENCE: 6
tcgtaccgtg agtaataatg cg                                              22

<210> SEQ ID NO 7
<211> LENGTH: 22
<212> TYPE: DNA
<213> ORGANISM: artificial sequence
<220> FEATURE:
<223> OTHER INFORMATION: primer

<400> SEQUENCE: 7
tccttcattc caccggagtc tg                                              22

<210> SEQ ID NO 8
<211> LENGTH: 22
<212> TYPE: DNA
<213> ORGANISM: artificial sequence
<220> FEATURE:
<223> OTHER INFORMATION: primer

<400> SEQUENCE: 8
ctgtgcgtgt gacagcggct ga                                              22

<210> SEQ ID NO 9
<211> LENGTH: 21
<212> TYPE: DNA
<213> ORGANISM: artificial sequence
<220> FEATURE:
<223> OTHER INFORMATION: primer

<400> SEQUENCE: 9
gtcaggtgaa gtgaaggaca a                                               21

<210> SEQ ID NO 10

```
<211> LENGTH: 21
<212> TYPE: DNA
<213> ORGANISM: artificial sequence
<220> FEATURE:
<223> OTHER INFORMATION: primer

<400> SEQUENCE: 10
ctggtacagc caagggtaaa t                                               21

<210> SEQ ID NO 11
<211> LENGTH: 22
<212> TYPE: DNA
<213> ORGANISM: artificial sequence
<220> FEATURE:
<223> OTHER INFORMATION: primer

<400> SEQUENCE: 11
ccttcagagc tgagaggtac ta                                              22

<210> SEQ ID NO 12
<211> LENGTH: 22
<212> TYPE: DNA
<213> ORGANISM: artificial sequence
<220> FEATURE:
<223> OTHER INFORMATION: primer

<400> SEQUENCE: 12
ctcaaactcc tcttgggctt ta                                              22
```

METHODS OF DETECTING LUNG CANCER

CROSS-REFERENCE TO RELATED APPLICATIONS

This application claims the benefit of U.S. Provisional Appl. No. 62/482,222, filed Apr. 6, 2017, the contents of which are hereby incorporated by reference in their entirety.

STATEMENT OF FEDERALLY SPONSORED RESEARCH AND DEVELOPMENT

This invention was made with government support under Grant Number CA205746 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 10,570 Byte ASCII (Text) file named "Sequence_Listing_ST25.txt," created on Apr. 5, 2018.

FIELD OF THE INVENTION

The field of the invention relates to lung cancer biology. In particular, the field of the invention relates to the diagnosis and prognosis thereof.

BACKGROUND OF THE INVENTION

Lung cancer is the leading cancer killer worldwide, of which more than 85% are non-small cell lung cancer (NSCLC). Tobacco smoking is the major cause of NSCLC. A NCI-National Lung Screening Trial (NLST) showed that the early detection of lung cancer using low-dose CT (LDCT) can significantly reduce mortality rates (Aberle, et al., *N Engl J Med* 365: 395-409, 2011). LDCT is now used for lung cancer screening in smokers (Moyer V A., *Ann Intern Med* 160: 330-8, 2014). However, LDCT is associated with over-diagnosis, excessive cost, and radiation exposure (Patz E F, Jr., et al., *JAMA Intern Med* 174: 269-74, 2014; Aberle, et al., *N Engl J Med* 365: 395-409, 2011). The CT scan has dramatically increased the number of indeterminate pulmonary nodules (PNs) in asymptomatic individuals. 24.2% of heavy smokers had indeterminate PNs detected by LDCT, whereas 96.4% of these PNs were ultimately confirmed as benign growths (Patz E F, Jr., et al., *JAMA Intern Med* 174: 269-74, 2014). The development of non-invasive or circulating biomarkers that can accurately and cost-effectively diagnose early stage lung cancer is required (Hubers A J, et al., *Br J Cancer* 109(3): 530-537, 2013).

During tumor development, cancer cells undergo apoptosis and necrosis, and release tumor-associated molecules that can circulate in the bloodstream. The tumors-derived molecules in plasma may provide cell-free circulating cancer biomarkers. Numerous plasma biomarkers have been developed by detecting the circulating cell-free DNA, gene methylated products, proteins, and metabolites for lung cancer early detection (Hubers A J, et al., *Br J Cancer* 109(3): 530-537, 2013). However, due to low sensitivity rates for diagnosis, none of them has been well accepted in clinics (Hubers A J, et al., *Br J Cancer* 109(3): 530-537, 2013). For instance, a blood test (Cancer-SEEK) was recently developed that could detect eight common cancer types by determining circulating proteins and mutations of cell-free DNA (Cohen J D, et al., *Science* 359(6378): 926-930, 2018). However, the test had about 60% sensitivity for diagnosis of all stages of lung cancer and only 40% sensitivity for the stage I disease (Cohen J D, et al., *Science* 359(6378): 926-930, 2018).

MicroRNAs (miRNAs) are small non-coding RNA molecules (containing about 22 nucleotides) that function as posttranscriptional regulators of gene expression. Dysregulation of miRNAs plays a crucial role in lung tumorigenesis (Costa F F, *Gene* 357: 83-94, 2005; Yanaihara N, et al., *Cancer Cell* 9: 189-98, 2006; Shen J, Jiang F, *Expert Opin Med Diagn* 6: 197-207, 2012; Mitchell P S, et al., *Proc Natl Acad Sci USA* 105: 10513-8, 2008). Due to their small size and relative resistance to nucleases, miRNAs are highly stable in peripheral plasma which is an easily accessible and rich biological fluid (Mitchell P S, et al., *Proc Natl Acad Sci USA* 105: 10513-8, 2008). Plasma miRNAs that are directly released from primary lung tumors or the circulating lung cancer cells might provide circulating biomarkers for lung cancer (Mitchell P S, et al., *Proc Natl Acad Sci USA* 105: 10513-8, 2008). Numerous miRNAs have been identified as diverse panels of biomarkers, which, however, produce widespread inconsistent results in lung cancer diagnosis (Shen J, et al., *Lab Invest* 91: 579-87, 2011; Chen X, et al., *Cell Res* 18: 997-1006, 2008). Furthermore, sensitivities and specificities of these plasma miRNA biomarkers are not high enough to be used in the clinical settings for predicting malignancy among indeterminate PNs (Shen J, Jiang F, *Expert Opin Med Diagn* 6: 197-207, 2012).

Long non-coding RNAs (lncRNAs) have minimum transcript length of 200 bp and play vital roles in various biological processes (Ma, L., et al., *RNA Biol* 10: 925-933, 2013). lncRNAs can regulate different molecular signaling pathways via changing gene expression, and therefore, their dysregulations are implicated in numerous mechanisms of carcinogenesis (Meseure, D., et al., *Biomed Res Int* 320214, 2015; Prensner, J. R., and Chinnaiyan, A. M., *Cancer Discov* 1, 391-407, 2011). Dysregulation of some lncRNAs has been found in relation to oncogenesis and metastasis of lung tumor (Zhou, M., et al., *J Transl Med* 13, 231, 2015; Li, M., et al., *Tumour Biol* 36, 9969-9978, 2015; Schmidt, L., et al., *J Thorac Oncol* 6, 1984-1992, 2011). Importantly, plasma lncRNAs directly released from primary tumors or the circulating cancer cells might provide biomarkers for human malignancies (Liang, W, et al., *Medicine (Baltimore)* 95, e4608, 2016).

To date, several plasma lncRNAs have been identified that show the potential for distinguishing lung cancer patients from non-cancer subjects (Zhu, Q., et al., *J Cell Mol Med* 21, 2184-2198, 2017). Yet none of them has been accepted in the clinical settings for lung cancer diagnosis, mainly due to the low sensitivity and specificity. Recent studies have characterized 21 lncRNAs whose aberrations are associated with lung cancer (Li, M., et al., *Tumour Biol* 36, 9969-9978, 2015). Furthermore, using whole-genomic next generation sequencing (NGS) to analyze ncRNA profile of primary lung tumor tissues, five additional lung cancer-related lncRNAs were identified (Ma, J., et al., *Mol Oncol* 8, 1208-1219, 2014; Gao, L., et al., *Int J Cancer* 136, E623-629, 2015). These lung tumor-associated lncRNAs may provide a comprehensive list of biomarker candidates for developing circulating lung cancer biomarkers.

Glycosylation is one of the most abundant protein modifications, and involved in major physiological events, including cell differentiation, proliferation, trafficking, migration and intracellular and intercellular signaling. Gathering evidences have demonstrated that aberrant glycosylation is the result of alterations in glycosyltransferases that play crucial in the development and progression of carcinogenesis (Chachadi V B, et al., *Glycobiology* 25(9): 963-975, 2015). Fucosylation is the major type of glycosylation and regulated by fucosyltransferases (FUTs), which catalyze the transfer of the fucose residue from GDP-fucose donor substrate to acceptor substrates present on oligosaccharides, glycoproteins and glycolipids (Wu L H, et al., *Glycobiology* 20(2): 215-223, 2010). Aberrant fucosylation is associated with malignant transformation.

There are 13 different FUTs, including FUT1 to 11, protein O-fucosyltransferase 1 (POFUT1), and POFUT2 (Zhou W, et al., *Oncotarget* 8(57): 97246-97259, 2017; Sullivan F X, et al., *J Biol Chem* 273(14): 8193-8202, 1998). Abnormal protein expression of FUTs has been proven to associate the development and progression of malignancies, including lung cancer (Zhou W, et al., *Oncotarget* 8(57): 97246-97259, 2017; Watanabe K, et al., *Surg Today* 46(10): 1217-1223, 2016; Honma R, et al., *Oncology* 88(5): 298-308, 2015; Noda K, et al., *Hepatology* 28(4): 944-952, 1998). Furthermore, studying glycans and glycan-binding proteins has shown that changes in fucosylation of glycoproteins were potential cancer biomarkers. For example, increased fucosylated alpha-fetoprotein (AFP) level is observed in sera of patients with hepatocellular carcinoma. AFP is one of the most representative types of glycan-related cancer biomarkers (Breborowicz J, et al., *Scand J Immunol* 14(1): 15-20, 1981; Aoyagi Y, et al., *Cancer* 67(9): 2390-2394, 1991). However, AFP is also elevated in sera of patients with various benign diseases such as accurate and chronic hepatitis (Taniguchi N and Kizuka Y, *Adv Cancer Res* 126: 11-51, 2015). Therefore, the fucosylated glycoproteins-based circulating biomarkers exhibit an insufficient value in the diagnosis of malignancies.

There is a significant need for new, non-invasive screening techniques for detecting pulmonary nodules and lung cancer tumors. There is also a significant need to develop techniques with greater sensitivity and specificity than techniques currently available.

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

In one aspect, the invention provides a method of predicting whether a pulmonary nodule in a subject is benign or non-small cell lung cancer, comprising
   a. obtaining the results of an assay that measures an expression level of miR205-5p in a plasma sample from the subject;
   b. obtaining the results of an assay that measures an expression level of miR126 in a plasma sample from the subject;
   c. obtaining the results of an assay that provides a size of the pulmonary nodule in the subject; and
   d. calculating a probability value based on the combination of the expression levels of miR205-5p and miR126, and the size of the pulmonary nodule,
wherein if the probability value exceeds a specified threshold, the pulmonary nodule is predicted as non-small cell lung cancer.

In another aspect, the invention provides use of miR205-5p and miR126 as biomarkers in combination with size of a pulmonary nodule for predicting non-small cell lung cancer in a subject.

In another aspect, the invention provides a kit comprising one or more reagents for detection of miR205-5p and miR126 from a sample.

In another aspect, the invention provides a non-invasive method for assessing efficacy of a treatment in a subject diagnosed with non-small cell lung cancer, comprising:
   a. obtaining the results of an assay that measures an expression level of miR205-5p in a plasma sample from the subject;
   b. obtaining the results of an assay that measures an expression level of miR126 in a plasma sample from the subject;
   c. obtaining the results of an assay that provides a size of the pulmonary nodule in the subject; and
   d. generating a receiver operating characteristic (ROC) curve and calculating an area under the ROC curve (AUC), said area under the curve (AUC) comprising a first comparator value;
   e. administering a treatment for non-small cell lung cancer to the subject;
   f. repeating steps a) to d) to calculate a second AUC value;
   g. comparing the second AUC value to the first comparator value; wherein a lesser second AUC value indicates that the selected treatment is efficacious against the non-small cell lung cancer.

In another aspect, the invention provides a method for predicting the presence of non-small cell lung cancer in a subject, comprising
   a. obtaining the results of an assay that measures an expression level of miR-210 in a plasma sample from the subject;
   b. obtaining the results of an assay that measures an expression level of FUT8 in a plasma sample from the subject;
   c. obtaining the results of an assay that measures an expression level of SNHG1;
   d. calculating a probability value based on the combination of the expression levels of miR-210, FUT8, and SNHG1,
wherein if the probability value exceeds a specified threshold, the subject is predicted to have lung cancer.

In another aspect, the invention provides use of the combination of miR210, FUT8 and SNHG1 for predicting lung cancer in a subject.

In another aspect, the invention provides a kit comprising one or more reagents for detection of miR210, FUT8 and SNHG1 from a sample.

In another aspect, the invention provides a non-invasive method for assessing efficacy of a treatment in a subject diagnosed with lung cancer, comprising:
   a. obtaining the results of an assay that measures an expression level of miR210 in a plasma sample from the subject;
   b. obtaining the results of an assay that measures an expression level of FUT8 in a plasma sample from the subject;
   c. obtaining the results of an assay that measures an expression level of SNHG1;

d. generating a receiver operating characteristic (ROC) curve and calculating an area under the ROC curve (AUC), said area under the curve (AUC) comprising a first comparator value;
e. administering a treatment for lung cancer to the subject;
f. repeating steps a) to d) to calculate a second AUC value;
g. comparing the second AUC value to the first comparator value; wherein a lesser second AUC value indicates that the treatment is efficacious against lung cancer.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 8. Microarray analysis showed that 11 miRNAs displayed a significantly different level in plasma samples of patients with malignant PNs versus individuals with benign diseases.

DETAILED DESCRIPTION OF THE INVENTION

Figure 1:
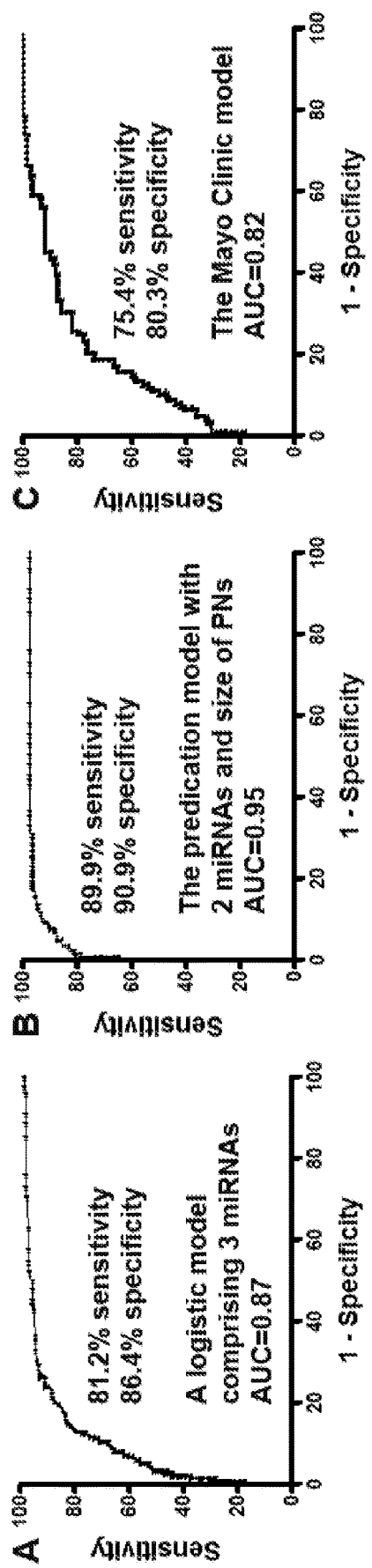
FIG. 1. Receiver-operator characteristic (ROC) curve analysis of the classifier, panel of the three plasma miRNA biomarkers, and Mayo Clinic model for distinguishing malignant from benign PNs in a training set of patients. The area under the ROC curve (AUC) for each approach conveys its accuracy for diagnosis of malignant PNs. The classifier (probability value=8687+1.5172×log(copy number of miR205-5p/µl plasma sample)−2.5117×log(copy number of miR-126/µl plasma sample)+0.8262×diameter of pulmonary nodule in centimeters) produces a higher AUC value (B) for identifying malignant PNs, compared with the panel of the three plasma miRNA biomarkers (miRs-126, 210, and 205-5p) (A) and Mayo Clinic model (C) (All P<0.05).

It is shown herein that plasma expression levels of miR205-5p and miR126 in combination with pulmonary nodule size can be useful to predict whether a pulmonary nodule is benign or is non-small cell lung cancer. It is also shown herein that plasma expression levels of miR-210, FUT8, and the long non-coding RNA (lncRNA) SNHG1 can be useful to predict whether a subject, such as a heavy smoker, has lung cancer.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

In some embodiments, the practice of the present invention employs various techniques of molecular biology (including recombinant techniques), microbiology, cell biology, biochemistry and immunology. See, e.g., Sambrook et al. *Molecular Cloning: A Laboratory Manual*, $2^{nd}$ edition (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR 2: A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "an antibody" includes a plurality of antibodies, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

In one embodiment, the invention provides for the use of miR205-5p and miR126 as biomarkers in combination with size of a pulmonary nodule for predicting and/or diagnosing lung cancer in a subject. The present invention also provides a method for determining a prognosis of a lung cancer patient. In some embodiments, the size of the pulmonary nodule and the markers miR205-5p and miR126 are quantified in a plasma sample obtained after a subject is diagnosed with lung cancer. Periodic analysis of the biomarkers and nodule size in the subject are useful in determining the aggressiveness of an identified cancer as well as its likelihood of responding to a given treatment.

In another embodiment, the invention provides for the use of a combination of miR210, FUT8 and lncRNA (SNHG1) for predicting and/or diagnosing non-small cell lung cancer in a subject. The present invention also provides a method for determining a prognosis of a lung cancer patient. In some embodiments, the markers miR210, FUT8 and lncRNA (SNHG1) are quantified in a plasma sample obtained after a subject is diagnosed with lung cancer. Periodic analysis of the biomarkers and nodule size in the subject are useful in determining the aggressiveness of an identified cancer as well as its likelihood of responding to a given treatment.

In another embodiment, the invention provides a method of predicting whether a pulmonary nodule in a subject is benign or non-small cell lung cancer, comprising
  a. obtaining the results of an assay that measures an expression level of miR205-5p in a plasma sample from the subject;
  b. obtaining the results of an assay that measures an expression level of miR126 in a plasma sample from the subject;
  c. obtaining the results of an assay that provides a size of the pulmonary nodule in the subject; and
  d. calculating a probability value based on the combination of the expression levels of miR205-5p and miR126, and the size of the pulmonary nodule,
wherein if the probability value exceeds a specified threshold, the pulmonary nodule is predicted as non-small cell lung cancer.

In another embodiment, the present invention also provides for a method of identifying a subject as having a poor prognosis for non-small cell lung cancer, the method comprising
  a. obtaining the results of an assay that measures an expression level of miR205-5p in a plasma sample from the subject;
  b. obtaining the results of an assay that measures an expression level of miR126 in a plasma sample from the subject;
  c. obtaining the results of an assay that provides a size of the pulmonary nodule in the subject;
  d. calculating a first probability value based on the combination of the expression levels of miR205-5p and miR126, and the size of the pulmonary nodule;
  e. repeating steps a-c. after a period of time and calculating a second probability value based on the combination of the expression levels of miR205-5p and miR126, and the size of the pulmonary nodule; and
  f. comparing the first and second probability values,
wherein if the second probability value is greater than the first probability value, the subject has a poor prognosis for non-small cell lung cancer.

In another embodiment, the invention provides a non-invasive method for assessing efficacy of a treatment in a subject diagnosed with non-small cell lung cancer, comprising:
  a. obtaining the results of an assay that measures an expression level of miR205-5p in a plasma sample from the subject;
  b. obtaining the results of an assay that measures an expression level of miR126 in a plasma sample from the subject;
  c. obtaining the results of an assay that provides a size of the pulmonary nodule in the subject; and
  d. generating a receiver operating characteristic (ROC) curve and calculating an area under the ROC curve (AUC), said area under the curve (AUC) comprising a first comparator value;
  e. administering a treatment for non-small cell lung cancer to the subject;
  f. repeating steps a) to d) to calculate a second AUC value;
  g. comparing the second AUC value to the first comparator value; wherein a lesser second AUC value indicates that the selected treatment is efficacious against the non-small cell lung cancer.

In another embodiment, the invention provides a method of detecting miR205-5p and miR126 in a subject, comprising
  a. obtaining a plasma sample from the subject; and
  b. detecting whether miR205-5p and miR126 are present in the sample by measuring the expression level of miR205-5p and miR126 in the plasma sample.

In another embodiment, the invention provides a method for predicting the presence of non-small cell lung cancer in a subject, comprising
  a. obtaining the results of an assay that measures an expression level of miR-210 in a plasma sample from the subject;
  b. obtaining the results of an assay that measures an expression level of FUT8 in a plasma sample from the subject;
  c. obtaining the results of an assay that measures an expression level of SNHG1;
  d. calculating a probability value based on the combination of the expression levels of miR-210, FUT8, and SNHG1,
wherein if the probability value exceeds a specified threshold, the subject is predicted to have lung cancer.

In another embodiment, the present invention also provides for a method of identifying a subject as having a poor prognosis for non-small cell lung cancer, the method comprising
  b. obtaining the results of an assay that measures an expression level of miR-210 in a plasma sample from the subject;
  c. obtaining the results of an assay that measures an expression level of FUT8 in a plasma sample from the subject;
  d. obtaining the results of an assay that measures an expression level of SNHG1;
  e. calculating a first probability value based on the combination of the expression levels of miR-210, FUT8, and SNHG1;
  f. repeating steps a-c. after a period of time and calculating a second probability value based on the combination of the expression levels of miR-210, FUT8, and SNHG1; and
  g. comparing the first and second probability values
wherein if the second probability value is greater than the first probability value, the subject has a poor prognosis for lung cancer.

In another embodiment, the invention provides a non-invasive method for assessing efficacy of a treatment in a subject diagnosed with non-small cell lung cancer comprising:
  a. obtaining the results of an assay that measures an expression level of miR210 in a plasma sample from the subject;
  b. obtaining the results of an assay that measures an expression level of FUT8 in a plasma sample from the subject;
  c. obtaining the results of an assay that measures an expression level of SNHG1;
  d. generating a receiver operating characteristic (ROC) curve and calculating an area under the ROC curve (AUC), said area under the curve (AUC) comprising a first comparator value;
  e. administering a treatment for lung cancer to the subject;
  f. repeating steps a) to d) to calculate a second AUC value;
  g. comparing the second AUC value to the first comparator value; wherein a lesser second AUC value indicates that the treatment is efficacious against lung cancer.

In another embodiment, the invention provides a method of detecting miR210, FUT8, and SNHG1 in a subject, comprising
  a. obtaining a plasma sample from the subject; and
  b. detecting whether miR210, FUT8, and SNHG1 are present in the sample by measuring the expression level of miR210, FUT8, and SNHG1 in the plasma sample.

In some embodiments, the pulmonary nodule that is non-small cell lung cancer is an adenocarcinoma, squamous cell carcinoma or large cell carcinoma.

In some embodiments, the methods and uses as described herein are non-invasive and demonstrate an improvement in early detection over traditional methods such as low-dose computer tomography (LDCT). In some embodiments, only a plasma sample is required from a subject of interest to assay for expression levels of the polynucleotide markers described herein, although other biological fluids are contemplated.

In some embodiments, methods as described herein enable early detection. In some embodiments, the biomarkers function as an easy-to-perform assay for expression levels at a first screening to pre-identify subjects, such as smokers, for lung cancer. Subsequently screening the pre-identified individuals using CT imaging is costly way to diagnose lung cancer. Using the plasma biomarkers and pulmonary nodule size characteristics for specifically identifying lung cancer in a CT screening positive setting reduces the lung cancer-related mortality by i), sparing smokers with benign pulmonary nodules from the invasive biopsies and expensive follow-up examinations, ii) improving CT for precisely and preoperatively identifying lung cancer, and iii) facilitating effective treatments to be instantly initiated for lung cancer. As such, the methods of the invention are useful for risk assessment. The methods of the invention enable a quantitative, probabilistic method to determine when subjects, such as heavy smokers are predisposed to lung cancer. In some embodiments, the methods further comprise treating the cancer in the subject.

In some embodiments, calculating the probability of lung cancer comprises generating a receiver operating characteristic (ROC) curve; and calculating an area under the ROC curve (AUC), where the area under the curve (AUC) provides the probability of lung cancer in the subject. In some embodiments, the minimum statistically determined value of the probability is at least 80%. In some embodiments, the minimum statistically determined value of the probability is at least 0.80, at least 0.90, at least 0.91, at least 0.92, at least 0.93, at least 0.94, at least 0.95, at least 0.96, at least 0.97, at least 0.98, or at least 0.99.

In accordance with the methods of the invention, the expression levels of miR205-5p, miR126, miR-210, FUT8, and SNHG1 are determined in plasma samples. The methods of determining expression levels are not particularly limiting. In some embodiments, the expression levels are determined by quantitative RT-PCR. In some embodiments, the expression levels are determined by microarray or by a Northern blot. In some embodiments, the expression levels are determined by droplet digital PCR. In some embodiments, the methods comprise determining an absolute expression level in a sample without the need of a control, such as an internal control gene. In some embodiments, the methods comprise determining the expression levels of 1) miR205-5p and miR126; and/or 2) miR-210, FUT8, and SNHG1 alone, wherein the expression levels of other polynucleotides are not determined or assayed. In some embodiments, expression levels are not compared with expression levels in control plasma samples. In some embodiments, the expression levels are compared to a control plasma sample. In particular embodiments, the control sample is derived from a healthy subject. In other particular embodiments, the control sample is derived from the same subject at an earlier point in time.

As used herein, the term "subject" includes both human and animal subjects. In some embodiments, the term "subject" includes a human or other animal at risk of developing lung cancer or suffering from lung cancer. A subject can be, but is not limited to, a lung cancer patient, an undiagnosed smoker or other undiagnosed subject presenting with one or more symptoms associated with lung cancer or having pulmonary nodules not yet diagnosed as malignant. It also includes individuals who do not have lung cancer. Non-limiting examples of animal subjects include cats, dogs, rats, mice, swine, and primates. In some embodiments, the subject is a smoker, former smoker or non-smoker exposed to second hand smoke. In some embodiments, the subject has a smoking history selected from the group consisting of at least 15 pack-years, at least 20 pack-years, at least 25 pack-years at least 30 pack-years, at least 35 pack-years, at least 40 pack-years, at least 45 pack-years, at least 50 pack-years, at least 55 pack-years, at least 60 pack-years, and at least 65 pack-years. In some embodiments, the subject is at least 35 years old, at least 40 years old, at least 45 years old, at least 50 years old, at least 55 years old, at least 60 years old, or at least 65 years old. In some embodiments, the subject is between 55 and 80 years old. In some embodiments, the subject is between 55 and 80 years old and has a smoking history of at least 35 pack-years.

In some embodiments, the plasma sample is assayed for contaminating miRNA, that might arise, e.g., from blood cells. In some embodiments, the contaminating miRNA is selected from the group consisting of RBC-related miRNA (mir-451), myeloid-related miRNA (miR-223), lymphoid-associated miRNA (miR-150) and combinations thereof.

In some embodiments, miR-126 comprises SEQ ID NO:1 (NCBI Reference Sequence: NR_029695.1). In some embodiments, the expression level of miR-126 is assayed using 5'-TCGTACCGTGAGTAATAATGCG-3' (SEQ ID NO:6) as the forward primer and mRQ 3' primer (Clontech, Mountain View, Calif.) as the reverse primer.

In some embodiments, miR-205-5p comprises SEQ ID NO:2 (NCBI Reference Sequence: NR_029622.1). In some embodiments, the expression level of miR-205-5p is assayed using 5'-TCCTTCATTCCACCGGAGTCTG-3' (SEQ ID NO:7) as the forward primer and mRQ 3' primer (Clontech, Mountain View, Calif.) as the reverse primer.

In some embodiments, miR-210 comprises SEQ ID NO:3 (NCBI Reference Sequence: NR_029623.1). In some embodiments, the expression level of miR-210 is assayed using 5'-CTGTGCGTGTGACAGCGGCTGA-3' (SEQ ID NO:8) as the forward primer and mRQ 3' primer (Clontech, Mountain View, Calif.) as the reverse primer.

FUT8 corresponds to fucosyltransferase 8 polynucleotide sequence. In some embodiments, FUT8 comprises SEQ ID NO:4 (NCBI Reference Sequence: NM_178155.2 (2558-2655) 98 bp). In some embodiments, the expression level of FUT8 corresponding to nucleotides 2558-2655 of SEQ ID NO:4 is assayed using 5'-GTCAGGTGAAGT-GAAGGACAA-3' (SEQ ID NO:9) as the forward primer and 5'-CTGGTACAGCCAAGGGTAAAT-3' (SEQ ID NO:10) as the reverse primer.

In some embodiments, SNHG1 comprises SEQ ID NO:5 (NCBI Reference Sequence: NR_003098.1 (267-354) 88 bp). In some embodiments, the expression level of SNHG1 corresponding to nucleotides 267-354 of SEQ ID NO:5 is assayed using 5'-CCTTCAGAGCTGAGAGGTACTA-3' (SEQ ID NO:11) as the forward primer and 5'-CT-CAAACTCCTCTTGGGCTTTA-3' (SEQ ID NO:12) as the reverse primer.

In some embodiments, the probability value in the method of predicting whether a pulmonary nodule in a subject is benign or non-small cell lung cancer is calculated by a classifier having the following formula:

probability value=8687+1.5172×log(copy number of miR205–5p/µl plasma sample)−2.5117×log(copy number of miR-126/µl plasma sample)+0.8262× diameter of pulmonary nodule in centimeters.

In some embodiments, the classifier yields about 90% sensitivity and about 90% specificity for diagnosis of non-small cell lung cancer.

In some embodiments, if the probability value exceeds 0.85, the pulmonary nodule is predicted as non-small cell lung cancer. In some embodiments, if the probability value exceeds 0.90, the pulmonary nodule is predicted as non-small cell lung cancer. In some embodiments, if the probability value exceeds 0.95, the pulmonary nodule is predicted as non-small cell lung cancer. In some embodiments, if the probability value exceeds 0.99, the pulmonary nodule is predicted as non-small cell lung cancer.

In some embodiments, the probability value in the method of predicting the presence of lung cancer in a subject is calculated by a classifier having the following formula:

probability value=−7.29+2.8×log(copy number of SNHG1/µl plasma sample)+3.83×log(copy number of FUT8/µl plasma sample)+3.36×log(copy number of miR-210/µl plasma sample).

In some embodiments, the classifier yields about 95% sensitivity and about 95% specificity for diagnosis of lung cancer.

In some embodiments, if the probability value exceeds 0.80, the presence of lung cancer is predicted in the subject. In some embodiments, if the probability value exceeds 0.90, the presence of lung cancer is predicted in the subject. In some embodiments, if the probability value exceeds 0.95, the presence of lung cancer is predicted in the subject. In some embodiments, if the probability value exceeds 0.99, the presence of lung cancer is predicted in the subject.

In the above formulas, copy number refers to the number of molecules present in the sample volume.

In some embodiments, if the subject is diagnosed with lung cancer or non-small cell lung cancer, the methods further comprise treating the cancer. In some embodiments, the treatment is selected from administration of a therapeutic agent, surgery, radiofrequency ablation, radiation, and combinations thereof.

As used herein, the terms "treatment" or "treating" relate to any treatment of a condition of interest (e.g., lung cancer), including but not limited to therapeutic treatment, which can include inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

Therapeutic agents used in accordance with the invention are typically administered in an effective amount to achieve the desired response. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. In some embodiments, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

A dosing schedule may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art. In some embodiments, the therapeutic agent is administered in a dose of between about 0.01 mg/kg to about 100 mg/kg body weight. In some embodiments, the dose administered is about 1-50 mg/kg body weight of the subject. In some embodiments, the dose administered is about 5-25 mg/kg body weight of the subject. In some embodiments, the dose administered is about 10 mg/kg body weight of the subject.

In some embodiments, the therapeutic agent is a chemotherapeutic agent. In some embodiments, the chemotherapeutic agent is selected from the group consisting of cisplatin, carboplatin, paclitaxel (Taxol), albumin-bound paclitaxel (nab-paclitaxel, Abraxane), docetaxel (Taxotere), gemcitabine (Gemzar), vinorelbine (Navelbine), irinotecan (Camptosar), etoposide (VP-16), vinblastine, pemetrexed (Alimta), and combinations thereof.

In some embodiments, the therapeutic agent is selected from the group consisting of bevacizumab (Avastin), ramucirumab (Cyramza), erlotinib (Tarceva), afatinib (Gilotrif), gefitinib (Iressa), osimertinib (Tagrisso), necitumumab (Portrazza), crizotinib (Xalkori), ceritinib (Zykadia), alectinib (Alecensa), brigatinib (Alunbrig), dabrafenib (Tafinlar), trametinib (Mekinist), nivolumab (Opdivo), pembrolizumab (Keytruda), atezolizumab (Tecentriq), durvalumab (Imfinzi), and combinations thereof.

In some embodiments, the radiation is selected from the group consisting of external beam radiation therapy and brachytherapy (internal radiation therapy).

In another embodiment, the invention provides kits for diagnosing or prognosing lung cancer or characterizing the responsiveness of a subject having lung cancer to treatment. In some embodiments, the kit comprises one or more reagents for detection of miR205-5p and miR126 from a sample. In some embodiments, the kit comprises one or more reagents for detection of miR210, FUT8 and lncRNA from a sample, including polynucleotides comprising any or all of SEQ ID NOS:1-12 and mRQ 3' primer (Clontech, Mountain View, Calif.).

In some embodiments, a kit of the invention provides a reagent (e.g., primers as described herein) for measuring copy numbers or expression. If desired, the kit further comprises instructions for measuring copy number or expression and/or instructions for administering a therapy to a subject having lung cancer.

In particular embodiments, the instructions include at least one of the following: description of the therapeutic agent; dosage schedule and administration for treatment of lung cancer or symptoms thereof; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

In some embodiments, the kit comprises a sterile container which contains a therapeutic or diagnostic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1. A Classifier Integrating Plasma Biomarkers and Radiological Characteristics for Distinguishing Malignant from Benign Pulmonary Nodules Using microarray and droplet digital PCR to directly profile plasma miRNA expressions of 135 patients with PNs, 11 plasma miRNAs were identified that displayed a significant difference between patients with malignant versus benign PNs. Using multivariate logistic regression analysis of the molecular results and clinical/radiological characteristics, an integrated classifier was developed comprising two miRNA biomarkers and one radiological characteristic for distinguishing malignant from benign PNs. The classifier had 89.9% sensitivity and 90.9% specificity, being significantly higher compared with the biomarkers or clinical/radiological characteristics alone (All P<0.05). The classifier was validated in two independent sets of patients. It is shown for the first time that the integration of plasma biomarkers and radiological characteristics could more accurately identify lung cancer among indeterminate PNs. Future use of the classifier could spare individuals with benign growths from the harmful diagnostic procedures, while allowing effective treatments to be immediately initiated for lung cancer, thereby reduces the mortality and cost.

Numerous plasma miRNA biomarkers have been searched by detecting circulating miRNAs directly released from primary tumors or the circulating lung cancer cells, but have limited success, due to several challenges (Mitchell P S, Parkin R K, Kroh E M, et al. Circulating microRNAs as stable blood-based markers for cancer detection. Proc Natl Acad Sci USA, 105: 10513-8, 2008): 1), the release of contaminating miRNAs in plasma by hemolysis of blood cells always produces a low specificity with inconsistent results for cancer diagnosis. 2), since the amount of miRNAs directly derived from primary tumors in plasma is very low and further 'diluted' in a background of normal miRNAs (Mitchell P S, Parkin R K, Kroh E M, et al. Circulating microRNAs as stable blood-based markers for cancer detection. Proc Natl Acad Sci USA, 105: 10513-8, 2008), some cancer cell derived-miRNAs presenting at very low abundance in plasma are undetectable by RT-PCR, producing a very poor sensitivity for cancer detection (Whale A S, Huggett J F, Cowen S, et al. Comparison of microfluidic digital PCR and conventional quantitative PCR for measuring copy number variation. Nucleic Acids Res, 40: e82, 2012). 3), no standard endogenous control exists in plasma for normalizing circulating miRNAs, resulting in poor reproducibility and robustness among different studies. To address the challenges, first, in this study we use the EDRN-established SOPs for collecting and preparing blood specimens to reduce bias related to sampling methods, storage or purification, and to diminish the contamination of the blood cells-related miRNAs in plasma. Indeed, expression levels of blood cells-related miRNAs in our samples are negative, suggesting that there are no contaminated miRNAs from hemolysis of the blood cells. Second, we have demonstrated that ddPCR could directly and reliably quantify low abundance miRNAs in clinical samples with a higher sensitivity than conventional RT-PCR (Ma J, Li N, Guarnera M, et al. Quantification of Plasma miRNAs by Digital PCR for Cancer Diagnosis. Biomark Insights, 8: 127-36, 2013; Li N, Ma J, Guarnera M A, et al. Digital PCR quantification of miRNAs in sputum for diagnosis of lung cancer. J Cancer Res Clin Oncol, 140: 145-50, 2014). Furthermore, ddPCR can absolutely quantify copy number of miRNAs. In addition, ddPCR does not require external calibrators or endogenous control genes. Moreover, it is relatively resistant to PCR inhibitors. In this study we use ddPCR to analyze miRNAs in plasma. Our results show that miR-205-5p, a key lung tumor-specific miRNA presenting at a very low level unreliably detectable by RT-PCR in plasma (Shen J, Todd N W, Zhang H, et al. Plasma microRNAs as potential biomarkers for non-small-cell lung cancer. Lab Invest, 91: 579-87, 2011), is robustly and reproducibly quantified by ddPCR. Since ddPCR could reliably and sensitively measure the vital miRNAs that were not previously detectable in plasma using RT-PCR, our newly developed three miRNA biomarkers are not the same as the previous ones developed by using RT-PCR (Shen J, Jiang F. Applications of MicroRNAs in the Diagnosis and Prognosis of Lung Cancer. Expert Opin Med Diagn, 6: 197-207, 2012; Shen J, Todd N W, Zhang H, et al. Plasma microRNAs as potential biomarkers for non-small-cell lung cancer. Lab Invest, 91: 579-87, 2011; Shen J, Stass S A, Jiang F. MicroRNAs as potential biomarkers in human solid tumors. Cancer Lett, 329: 125-36, 2013; Shen J, Liu Z, Todd N W, et al. Diagnosis of lung cancer in individuals with solitary pulmonary nodules by plasma microRNA biomarkers. BMC Cancer, 11: 374, 2011). However, although using only three miRNAs, the logistic model has a higher specificity compared with a circulating miRNA signature composed by reciprocal ratios among 24 miRNAs (87% vs. 81%) for identifying lung cancer (Sozzi G, Conte D, Leon M, et al. Quantification of free circulating DNA as a diagnostic marker in lung cancer. J Clin Oncol, 21: 3902-8, 2003).

Previously, some models based on the clinical/radiological variables have shown the potential for predicting malignant PNs (Swensen S J, Silverstein M D, Ilstrup D M, et al. The probability of malignancy in solitary pulmonary nodules. Application to small radiologically indeterminate nodules. Arch Intern Med, 157: 849-55, 1997, Schultz E M, Sanders G D, Trotter P R, et al. Validation of two models to estimate the probability of malignancy in patients with solitary pulmonary nodules. Thorax, 63: 335-41, 2008; McWilliams A, Tammemagi M C, Mayo J R, et al. Probability of cancer in pulmonary nodules detected on first screening CT. N Engl J Med, 369: 910-9, 2013). Our present study confirms the previous findings that the clinical and radiological variables could be predictors for malignant PNs. However, the moderate sensitivity and specificity of these models limits the application in the clinical settings (Swensen S J, Silverstein M D, Ilstrup D M, et al. The probability of malignancy in solitary pulmonary nodules. Application to small radiologically indeterminate nodules. Arch Intern Med, 157: 849-55, 1997; Schultz E M, Sanders G D, Trotter P R, et al. Validation of two models to estimate the probability of malignancy in patients with solitary pulmonary nodules. Thorax, 63: 335-41, 2008). We reason that integrating plasma biomarkers with radiological/clinical characteristics might have a synergistic effect for identifying NSCLC among the indeterminate PNs. Indeed, by integrating the plasma biomarkers with radiological characteristics, we develop a classifier for distinguishing malignant from benign PNs. Although this simple classifier comprises only two biomarkers and one radiological variable of PNs, it has higher sensitivity and specificity compared with the panel of biomarkers or the Mayo Clinic model used alone. Furthermore, the performance of the classifier developed in White Americans and African Americas is confirmed in a geographically independent cohort (Chinese population), further implying the usefulness for detection of NSCLC among indeterminate PNs. In addition, the classifier with a simple equation and a single cut-off value would offer a convenient analytic means in the laboratory settings for the classification of malignant from benign PNs.

The areas for improvement do exist in the current study. A screening assay directed at a malignancy with an incidence≤5% should have a sensitivity exceeding 95% when the specificity is ≤95%, and vice versa. The incidence of lung cancer in heavy smokers is less than 3%, while LDCT has 90% sensitivity and only 61% specificity, producing a high false positive rate. Only the approaches with more than 95% specificity and appropriate sensitivity for identifying malignant PNs could supplement LDCT lung cancer screening. Although showing promise, our developed classifier with 89% sensitivity and 90% specificity does not hold the required performance. The two plasma miRNA biomarkers in the classifier were developed from the limited number of miRNAs identified by microarrays, however, by which other important lung cancer-associated miRNAs might not been included. We are using high-throughput next-generation sequencing to directly analyze plasma samples of patients with either malignant or benign PNs to identify new miRNA biomarkers for lung cancer. The performance of this classifier could be further improved by adding the new plasma miRNA biomarkers that are more specific to malignant PNs. Furthermore, the radiological features used in the study are obtained through the conventional image analysis that is based on subjective observation and limited to the measurements of nodule size in one dimension. Radiomics, an emerging technique extracting a large number of quantitative features from medical images automatically, provides a more detailed quantification of tumor phenotypic characteristics that have diagnostic value. In the future, we intend to incorporate the molecular biomarkers, radiomic features of nodules, and clinical characteristics of smokers to develop a classier that could more accurately and conveniently identify lung cancer among the indeterminate PNs.

In summary, we have for the first time developed a simple classifier by integrating plasma biomarkers with radiological characteristics that could identify lung cancer among indeterminate PNs. Future use of the classifier by sparing individuals with benign growths from the harmful diagnostic procedures, while allowing effective treatments to be immediately initiated for NSCLC, would complement LDCT for the early detection of lung cancer. Nevertheless, undertaking a prospective study to further validate the classifier for lung cancer in a large population-based LDCT screening positive setting among heavy smokers is required.

Materials and Methods

Patient Cohorts and Research Design

The study protocols were approved by the Institutional Review Boards of the University of Maryland Medical Center (UMMC), the Baltimore VA Medical Center (BVAMC), and Jiangsu Province Hospital of Traditional Chinese Medicine (JPHTCM). Inclusion criteria were current and former smokers who had CT-detected PNs and were between the ages of 55-74. Exclusion criteria included pregnancy or lactation, current pulmonary infection, thoracic surgery within 6 months, radiotherapy to the chest within 1 year, and life expectancy of <1 year. A PN was defined as a solitary, round, or oval lesion in the lung parenchyma in the absence of adenopathy, atelectasis, or pneumonia. We reviewed the medical records for their demographic and clinical variables about age, gender, race, ethnicity, history of cancer, and smoking behavior (smoking history, smoking status, pack years, and number of years since quitting). We also obtained radiographic characteristics of the PNs on CT images, including the maximum transverse size, the visually determined type (nonsolid or ground-glass opacity, part-solid, solid, perifissural, and spiculation), and the location in the lungs. A definitive malignant diagnosis was established and verified based on pathologic examination of tissues obtained via surgery or biopsy. A definitive benign diagnosis was established when a specific benign etiology was confirmed pathologically, or the PNs were clinically and radiographically stable after a 2-year follow-up with multiple examinations (MacMahon H, Austin J H, Gamsu G, et al. Guidelines for management of small pulmonary nodules detected on CT scans: a statement from the Fleischner Society. Radiology, 237: 395-400, 2005; Moyer V A. Screening for prostate cancer: U.S. Preventive Services Task Force recommendation statement. Ann Intern Med, 157: 120-34, 2012). The surgical pathologic staging was determined according to the TNM classification of the International Union Against Cancer with the American Joint Committee on Cancer and the International Staging System for Lung Cancer (Ohori M, Wheeler T M, Scardino P T. The New American Joint Committee on Cancer and International Union Against Cancer TNM classification of prostate cancer. Clinicopathologic correlations. Cancer, 74: 104-14, 1994). Histopathologic classification was determined according to the World Health Organization classification (Travis W D, Brambilla E, Nicholson A G, et al. The 2015 World Health Organization Classification of Lung Tumors: Impact of Genetic, Clinical and Radiologic Advances Since the 2004 Classification. J Thorac Oncol, 10: 1243-60, 2015). Altogether, we recruited 135, 126, and 98 patients with PNs from UMMC, BVAMC, and JPHTCM, respectively. Of the UMMC cohort, 69 had malignant PNs and were diagnosed with NSCLC, and 66 had benign PNs (Table 1). The 66 subjects with benign PNs were diagnosed with granulomatous inflammation (n=34), nonspecific inflammatory changes (n=23), or lung infections (n=9). From the UMMC cohort, we randomly selected 18 individuals with malignant PNs and 18 individuals with benign PNs, from whom, the plasma samples were analyzed by using a microarray to identify miRNA biomarker candidates for lung cancer. The identified miRNAs were then validated in all 135 plasma samples of the UMMC cohort by using droplet digital PCR (ddPCR). The resulted molecular data and clinical/radiological characteristics of the UMMC cohort of patients with PNs were analyzed to identify an optimal panel of biomarkers and then construct a classifier for identifying malignant PNs. 126 patients with PNs recruited from BVAMC were used as an independent testing cohort, while 98 patients with PNs recruited from JPHTCM were used an external testing cohort to confirm the classifier for the differentiation of malignant from benign PNs. The BVAMC cohort consisted of 63 patients with malignant PNs (NSCLC) and 63 patients with benign PNs (Table 2). The 63 subjects with benign PNs were diagnosed with granulomatous inflammation (n=30), nonspecific inflammatory changes (n=19), or lung infections (n=14). In the JPHTCM cohort, 49 had malignant PNs (NSCLC) and 49 had benign PNs. The 49 subjects with benign PNs were diagnosed with granulomatous inflammation (n=26), nonspecific inflammatory changes (n=17), or lung infections (n=6). The demographic and clinical parameters, including information about nodules size, of the three cohorts are shown in Tables 1-2.

TABLE 1

Characteristics of patients recruited in the University of Maryland Medical Center

| Characteristics | Patients with malignant PNs (n = 69) | Patients with benign PNs (n = 66) |
|---|---|---|
| Clinical | | |
| Age | 68.22 (SD 9.90) | 65.27 (SD 8.26) |
| Sex | | |
| Male | 46 | 45 |
| Female | 23 | 21 |

TABLE 1-continued

Characteristics of patients recruited in the University of Maryland Medical Center

| Characteristics | Patients with malignant PNs (n = 69) | Patients with benign PNs (n = 66) |
|---|---|---|
| Race | | |
| African American | 21 | 20 |
| White | 48 | 46 |
| Smoking history | | |
| Current smoker | 41 | 40 |
| Former smoker | 28 | 26 |
| Pack-years | 43.26 (SD 13.12) | 23.69 (SD 12.28) |
| Years quit | 7.16 (SD 4.69) | 12.69 (SD 8.27) |
| History of cancer | 7 | 2 |
| Stage of non-small cell cancer | | |
| Stage I | 18 | |
| Stage II | 18 | |
| Stage III-VI | 23 | |
| Histological type | | |
| AC | 33 | |
| SCC | 29 | |
| LC | 7 | |
| Radiological | | |
| Nodule size (mm) | 19.89 (SD 12.16) | 10.18 (SD 5.55) |
| Nodule Location | | |
| Left lower lobe | 9 | 13 |
| Left upper lobe | 25 | 18 |
| Right lower lobe | 15 | 20 |
| Right middle lobe | 4 | 7 |
| Right upper lobe | 15 | 8 |
| Nodule type (number) | | |
| Nonsolid or ground-glass opacity | 18 | 20 |
| Perifissural | 7 | 9 |
| Part-solid | 9 | 11 |
| Solid | 13 | 14 |
| Spiculation | 22 | 12 |

Abbreviations: PN, pulmonary nodule; SD, standard deviation; AC, adenocarcinoma; SCC, squamous cell carcinoma; LCC, large cell carcinoma.

TABLE 2

Characteristics of patients recruited in the Baltimore VA Medical Center

| Characteristics | Patients with malignant PNs (n = 63) | Patients with benign PNs (n = 63) |
|---|---|---|
| Clinical | | |
| Age | 67.38 (SD 9.16) | 64.48 (SD 9.01) |
| Sex | | |
| Male | 43 | 42 |
| Female | 20 | 21 |
| Race | | |
| African American | 19 | 20 |
| White | 44 | 43 |
| Smoking history | | |
| Current smoker | 40 | 39 |
| Former smoker | 23 | 24 |
| Pack-years | 44.67 (SD 12.19) | 25.78 (SD 13.19) |
| Years quit | 6.78 (SD 8.38) | 11.15 (SD 7.79) |
| History of cancer | 4 | 1 |

TABLE 2-continued

Characteristics of patients recruited in the Baltimore VA Medical Center

| Characteristics | Patients with malignant PNs (n = 63) | Patients with benign PNs (n = 63) |
|---|---|---|
| Stage of non-small cell cancer | | |
| Stage I | 20 | |
| Stage II | 19 | |
| Stage III-VI | 24 | |
| Histological type | | |
| AC | 31 | |
| SCC | 28 | |
| LC | 4 | |
| Radiological | | |
| Nodule size (mm) | 18.34 (SD 13.02) | 10.39 (SD 6.02) |
| Nodule Location | | |
| Left lower lobe | 8 | 11 |
| Left upper lobe | 21 | 17 |
| Right lower lobe | 15 | 20 |
| Right middle lobe | 5 | 7 |
| Right upper lobe | 14 | 8 |
| Nodule type (number) | | |
| Nonsolid or ground-glass opacity | 17 | 19 |
| Perifissural | 7 | 9 |
| Part-solid | 7 | 10 |
| Solid | 12 | 13 |
| Spiculation | 20 | 12 |

Abbreviations: PN, pulmonary nodule; SD, standard deviation; AC, 63 adenocarcinoma; SCC, squamous cell carcinoma; LCC, large cell carcinoma.

Blood Collection, Plasma Preparation, and RNA Isolation

The blood samples were collected before any treatment regimen. Variability in the blood collection and preparation might have confounding effects on the molecular analysis of the body fluid specimens. Furthermore, qualities of RNA samples are crucial for the accurate and robust measurement of plasma miRNAs. To reduce the variability and bias linked to sampling methods, storage or purification, in the three medical centers we collected blood and prepared plasma using the standard operating protocols (SOPs) developed by The National Cancer Institute Early Detection Research Network (EDRN) (Marks J R, Anderson K S, Engstrom P, et al. Construction and analysis of the NCI-EDRN breast cancer reference set for circulating markers of disease. Cancer Epidemiol Biomarkers Prev 2015; 24: 435-41; Tuck M K, Chan D W, Chia D, et al. Standard operating procedures for serum and plasma collection: early detection research network consensus statement standard operating procedure integration working group. J Proteome Res 2009; 8: 113-7). Furthermore, the release of contaminating miRNAs in plasma by hemolysis of blood cells such as red blood cells (RBCs) could yield nonspecific results. To avoid the contamination, we prepared plasma from blood within 2 hours after the collection as previously described (Shen J, Todd N W, Zhang H, et al. Plasma microRNAs as potential biomarkers for non-small-cell lung cancer. Lab Invest, 91: 579-87, 2011; Ma J, Li N, Guarnera M, et al. Quantification of Plasma miRNAs by Digital PCR for Cancer Diagnosis. Biomark Insights, 8: 127-36, 2013; Shen J, Liu Z, Todd N W, et al. Diagnosis of lung cancer in individuals with solitary pulmonary nodules by plasma microRNA biomarkers. BMC Cancer, 11: 374, 2011. Moreover, we used RBC lysis solution to maximally reduce the possible contamination from RBCs in plasma (Shen J, Stass S A, Jiang F. MicroRNAs as potential biomarkers in human solid tumors. Cancer Lett, 329: 125-36, 2013; Whale A S, Huggett J F, Cowen S, et al. Comparison of microfluidic digital PCR and conventional quantitative PCR for measuring copy number variation. Nucleic Acids Res, 40: e82, 2012; Li H, Jiang Z, Leng Q, et al. A prediction model for distinguishing lung squamous cell carcinoma from adenocarcinoma. Oncotarget, 11: 226-32, 2017; Liu H, Zhu L, Liu B, et al. Genome-wide microRNA profiles identify miR-378 as a serum biomarker for early detection of gastric cancer. Cancer Lett, 316: 196-203, 2012; Schisterman E F, Perkins N J, Liu A, et al. Optimal cut-point and its corresponding Youden Index to discriminate individuals using pooled blood samples. Epidemiology, 16: 73-81, 2005; Hanley J A, McNeil B J. A method of comparing the areas under receiver operating characteristic curves derived from the same cases. Radiology, 148: 839-43, 1983; Sozzi G, Conte D, Leon M, et al. Quantification of free circulating DNA as a diagnostic marker in lung cancer. J Clin Oncol, 21: 3902-8, 2003). We extracted RNA from plasma by using a protocol with miRNeasy Mini Kit spin column as described in our published work (Shen J, Jiang F. Applications of MicroRNAs in the Diagnosis and Prognosis of Lung Cancer. Expert Opin Med Diagn, 6: 197-207, 2012; Shen J, Todd N W, Zhang H, et al. Plasma microRNAs as potential biomarkers for non-small-cell lung cancer. Lab Invest, 91: 579-87, 2011; Shen J, Liao J, Guarnera M A, et al. Analysis of MicroRNAs in sputum to improve computed tomography for lung cancer diagnosis. J Thorac Oncol, 9: 33-40, 2014; Shen J, Stass S A, Jiang F. MicroRNAs as potential biomarkers in human solid tumors. Cancer Lett, 329: 125-36, 2013; Ma J, Li N, Guarnera M, et al. Quantification of Plasma miRNAs by Digital PCR for Cancer Diagnosis. Biomark Insights, 8: 127-36, 2013; Shen J, Liu Z, Todd N W, et al. Diagnosis of lung cancer in individuals with solitary pulmonary nodules by plasma microRNA biomarkers. BMC Cancer, 11: 374, 2011; Su Y, Fang H, Jiang F. Integrating DNA methylation and microRNA biomarkers in sputum for lung cancer detection. Clin Epigenetics, 8: 109, 2016; Su Y, Guarnera M A, Fang H, et al. Small non-coding RNA biomarkers in sputum for lung cancer diagnosis. Mol Cancer, 15: 36, 2016; Su J, Anjuman N, Guarnera M A, et al. Analysis of Lung Flute-collected Sputum for Lung Cancer Diagnosis. Biomark Insights, 10: 55-61, 2015; Su J, Liao J, Gao L, et al. Analysis of small nucleolar RNAs in sputum for lung cancer diagnosis. Oncotarget, 7: 5131-42, 2016; Xing L, Su J, Guarnera M A, et al. Sputum microRNA biomarkers for identifying lung cancer in indeterminate solitary pulmonary nodules. Clin Cancer Res, 21: 484-9, 2015; Li N, Ma J, Guarnera M A, et al. Digital PCR quantification of miRNAs in sputum for diagnosis of lung cancer. J Cancer Res Clin Oncol, 140: 145-50, 2014; Anjuman N, Li N, Guarnera M, et al. Evaluation of lung flute in sputum samples for molecular analysis of lung cancer. Clin Transl Med, 2: 15, 2013; Yu L, Todd N W, Xing L, et al. Early detection of lung adenocarcinoma in sputum by a panel of microRNA markers. Int J Cancer, 127: 2870-8, 2010; Xing L, Todd N W, Yu L, et al. Early detection of squamous cell lung cancer in sputum by a panel of microRNA markers. Mod Pathol, 23: 1157-64, 2010; Xie Y, Todd N W, Liu Z, et al. Altered miRNA expression in sputum for diagnosis of non-small cell lung cancer. Lung Cancer, 67: 170-6, 2010; Cao X, Wu Z, Jiang F, et al. Identification of chilling stress-responsive tomato microRNAs and their target genes by high-throughput sequencing and degradome analysis. BMC Genomics, 15: 1130, 2014; Li P, Zhang Q, Wu X, et al. Circulating microRNAs serve as novel biological markers for intracranial aneurysms. J Am Heart Assoc, 3: e000972, 2014; Huang Y, Yang S, Zhang J, et al. MicroRNAs as promising biomarkers for diagnosing human cancer. Cancer Invest, 28: 670-1, 2010; Ma J, Li N, Lin Y, et al. Circulating Neutrophil MicroRNAs as Biomarkers for the Detection of Lung Cancer. Biomark Cancer, 8: 1-7, 2016).

In addition, we analyzed expression levels of RBC-related miRNA (mir-451), myeloid-related miRNA (miR-223), and lymphoid-associated miRNA (miR-150) in all the RNA samples. The samples that were positive to these blood cells-related miRNAs were excluded from the study. RNA was immediately stored at −80 in a barcoded cryotube until use.

Microarray Analysis

The plasma RNA specimens were analyzed for miRNA expressions by using "Exiqon Services" (Exiqon, Denmark) with an established protocol as described in our previous reports (Ma J, Li N, Lin Y, et al. Circulating Neutrophil MicroRNAs as Biomarkers for the Detection of Lung Cancer. Biomark Cancer 2016; 8: 1-7; Ma J, Lin Y, Zhan M, et al. Differential miRNA expressions in peripheral blood mononuclear cells for diagnosis of lung cancer. Lab Invest 2015; 95: 1197-206).

Briefly, 6 µl RNA was reversely transcribed in 30 µl reactions using the miRCURY LNA™ Universal RT miRNA PCR, Polyadenylation and cDNA synthesis kit (Exiqon). cDNA was diluted 100× and assayed in 10 ul PCR reactions according to the protocol for miRCURY LNA™ Universal RT miRNA PCR. Each miRNA was assayed by qPCR on the miRNA Ready-to-Use PCR, Haman Panels I using ExiLENT SYBR® Green master mix. Negative controls excluding template from the reverse transcription reaction were performed and profiled like the samples. The amplification was performed in a LightCycler® 480 Real-Time PCR System (Roche, San Francisco, Calif.) in 384 well plates. The amplification curves were made by using quantification cycle (Cq), which was used as a relative value for further quantification of the tested genes. We normalized the resulted data by using the average of assays detected in the samples (average-assay Cq).

Droplet Digital PCR (ddPCR)

ddPCR analysis for quantification of miRNAs was done as described in our published studies (Ma J, Li N, Guarnera M, et al. Quantification of Plasma miRNAs by Digital PCR for Cancer Diagnosis. Biomark Insights, 8: 127-36, 2013; Li N, Ma J, Guarnera M A, et al. Digital PCR quantification of miRNAs in sputum for diagnosis of lung cancer. J Cancer Res Clin Oncol, 140: 145-50, 2014; Ma J, Mannoor K, Gao L, et al. Characterization of microRNA transcriptome in lung cancer by next-generation deep sequencing. Mol Oncol, 8: 1208-19, 2014).

Briefly, 1 ul RNA per sample was obtained for RT to produce cDNA by TaqMan miRNA RT Kit (Applied Biosystems, Foster City, Calif.) and specific primers for each gene. 20 µl reaction mixture containing 5 µl of cDNA solution, 10 µl Supermix, 1 µl of Taqman primer/probe mix was loaded into a cartridge with droplet Generation oil (Bio-Rad, Hercules, Calif.) and then placed into the QX100 Droplet Generator (Bio-Rad). The generated droplets were transferred to a 96-well PCR plate. PCR amplification was carried on a T100 thermal cycler (Bio-Rad). ddPCR was a direct method for quantitatively measuring nucleic acids (Li N, Ma J, Guarnera M A, et al. Digital PCR quantification of miRNAs in sputum for diagnosis of lung cancer. J Cancer Res Clin Oncol, 140: 145-50, 2014). The number of positive reactions, together with Poisson's distribution, were used to produce a straight and high-confidence measurement of the original target concentration (Whale A S, Huggett J F, Cowen S, et al. Comparison of microfluidic digital PCR and conventional quantitative PCR for measuring copy number variation. Nucleic Acids Res, 40: e82, 2012). Therefore, ddPCR could absolutely quantify targeted nucleic acid sequences without requiring external calibrators or endogenous controls (genes) (Ma J, Li N, Guarnera M, et al. Quantification of Plasma miRNAs by Digital PCR for Cancer Diagnosis. Biomark Insights, 8: 127-36, 2013; Whale A S, Huggett J F, Cowen S, et al. Comparison of microfluidic digital PCR and conventional quantitative PCR for measuring copy number variation. Nucleic Acids Res, 40: e82, 2012; Li H, Jiang Z, Leng Q, et al. A prediction model for distinguishing lung squamous cell carcinoma from adenocarcinoma. Oncotarget, 11: 226-32, 2017). The plate was loaded on Droplet Reader (Bio-Rad), by which copy number of each miRNA per µl PCR reaction mixture was directly determined. All assays were performed in triplicates. Furthermore, two interplate controls and one no-template control were carried along in each experiment. The no template control for RT was RNease free water instead of RNA sample input, and no template control for PCR was RNease free water instead of RT products input.

Statistical Analysis

To identify plasma miRNAs that were differentially expressed in patients with malignant versus benign PNs, we expected the acceptable number of false positives to be 1.0, fold difference between cases and controls at 2.0, standard deviation of the gene measurements on the base-two logarithmic scale at 0.7, and desired power at 80%. Given 375 miRNAs included in the array, at least 15 specimens for each type of the patients were required to achieve the statistical criteria. Furthermore, based on one-sample with binomially distributed outcomes, we needed 45 cases from each group at 5% significant level with 80% power to discover and validate a panel of biomarkers or classifier for predicting malignant PNs. For analysis of microarray data, we performed an unpaired unequal variance t test with Benjamini-Hochberg correction (Liu H, Zhu L, Liu B, et al. Genome-wide microRNA profiles identify miR-378 as a serum biomarker for early detection of gastric cancer. Cancer Lett, 316: 196-203, 2012) to identify differentially expressed miRNAs in plasma of patients with malignant versus benign PNs. We used univariate analysis to determine which of plasma miRNAs and clinical and radiological variables were associated with malignant PNs. The significantly associated factors were then analyzed by using multivariate logistic regression models with constrained parameters as in least absolute shrinkage and selection operator (LASSO) based on receiver-operator characteristic (ROC) curve to identify an optimal panel of miRNA biomarkers and construct a classifier for malignant PNs. The optimal cutoff value was generated using the Youden index (Schisterman E F, Perkins N J, Liu A, et al. Optimal cut-point and its corresponding Youden Index to discriminate individuals using pooled blood samples. Epidemiology, 16: 73-81, 2005). The 95% confidence intervals in the ROC plot for proportions were estimated. To compare the performance of the classifier with that of the plasma biomarkers and the Mayo Clinic model (Swensen S J, Silverstein M D, Ilstrup D M, et al. The probability of malignancy in solitary pulmonary nodules. Application to small radiologically indeterminate nodules. Arch Intern Med, 157: 849-55, 1997), we used the method of Hanley and McNeil with the area under an ROC curve (AUC) analysis (Hanley J A, McNeil B J. A method of comparing the areas under receiver operating characteristic curves derived from the same cases. Radiology, 148: 839-43, 1983). The classifier was blindly validated in two additional sets of patients by comparing the calculated results with final clinical diagnosis and the AUCs.

Results

Identifying Differentially-Expressed miRNAs in Plasma of Patients with Malignant Versus Benign PNs Of the 375 miRNAs embodied on the miRNA array, 282 (75.2%) showed a <35 Cq value in all plasma specimens of 36 patients with either malignant (18) or benign (18) PNs. Furthermore, the miRNA expression levels measured by using the microarray in the replicates of each sample were highly correlated (all p<0.0001). Therefore, the 282 miR-NAs were reliably measurable in plasma of the patients with PNs. Among the miRNAs, 11 (miRs-21-5p, -103a-3p, -126-3p, -135a-5p, -145-5p, -141-3p,-193b-3p, -200b-3p, -205-5p, -210, and -301b) exhibited more than 2.0 fold-changes with a p<0.05 in plasma of patients with malignant versus benign PNs (Table 13). Of the 11 miRNAs, nine (miRs-21-5p, -103a-3p, -126, 141-3p,-193b-3p, -205-5p, 210, and -301b) had a higher expression level, whereas three (miRs-135a-5p, 145-5p, and -200b-3p) displayed a lower level in plasma of patients with malignant versus benign PNs (All P<0.05).

Validating the Changes of the Plasma miRNAs, and Developing miRNA Biomarkers for Malignant PNs The changes of 11 malignant PN-related plasma miRNAs identified by the microarray should be validated using a different and reliable technique (Shen J, Stass S A, Jiang F. MicroRNAs as potential biomarkers in human solid tumors. Cancer Lett, 329: 125-36, 2013). We demonstrated that ddPCR was a more sensitive technique with greater precision and reproducibility to detect expression of miRNAs in plasma than did the conventional reverse transcription PCR (RT-PCR) (Ma J, Li N, Guarnera M, et al. Quantification of Plasma miRNAs by Digital PCR for Cancer Diagnosis. Biomark Insights, 8: 127-36, 2013; Li N, Ma J, Guarnera M A, et al. Digital PCR quantification of miRNAs in sputum for diagnosis of lung cancer. J Cancer Res Clin Oncol, 140: 145-50, 2014). Moreover, ddPCR could absolutely and precisely determine copy number of miRNAs without the need of an internal control gene, such as U6. Therefore, we used ddPCR to assess changes of the 11 miRNAs in 135 plasma samples of the UMMC cohort. Each well of the plasma samples contained at least 10,000 droplets. By contrast, no product was synthesized in the negative control samples. Thus, the plasma samples were successfully "read" for the absolute quantification of the 11 miRNAs by using a reliable and accurate assay. ddPCR analysis showed that all the 11 miRNAs displayed a significantly different level in plasma samples of patients with malignant PNs versus individuals with benign diseases (all P<0.05). Furthermore, the miRNAs had consistent changes detected by ddPCR in the same direction as in the microarray analysis: nine displayed a higher expression level, whereas three exhibited a lower level in plasma of subjects with malignant versus benign PNs (Table 3).

TABLE 3

Expression levels of 11 plasma miRNAs and their diagnostic significance in 135 patients with malignant versus benign PNs

| miRNAs | Mean (SD) in patients with benign PNs | Mean (SD) in patients with malignant PNs | P-value | AUC (95% confidence interval) |
|---|---|---|---|---|
| miR-21-5p | 8.9893 (5.7922) | 18.9694 (23.4001) | 0.0458 | 0.6135 (0.5102 to 0.7168) |
| miR-103a-3p | 1.5987 (1.9266) | 7.0492 (14.2826) | 0.0386 | 0.6160 (0.5155 to 0.7166) |
| miR-126-3p | 4.6113 (4.5983) | 20.1927 (40.4664) | 0.0301 | 0.6075 (0.4977 to 0.7173) |
| miR-135a-5p | 0.0237 (0.0305) | 0.0123 (0.0180) | 0.0068 | 0.5696 (0.4784 to 0.6608) |
| miR-145-5p | 0.9343 (1.4553) | 0.7990 (1.4933) | 0.0004 | 0.6761 (0.5868 to 0.7655) |
| miR-141-3p | 0.0239 (0.0663) | 0.0481 (0.1143) | 0.0480 | 0.5962 (0.5064 to 0.6861) |
| miR-193b-3p | 0.0523 (0.0525) | 0.0772 (0.0810) | 0.0203 | 0.6318 (0.5468 to 0.7168) |
| miR-200b-3p | 0.0319 (0.0453) | 0.0151 (0.0190) | 0.0010 | 0.6199 (0.5330 to 0.7069) |
| miR-205-5p | 0.0114 (0.0191) | 0.0672 (0.1054) | <0.001 | 0.8187 (0.7503 to 0.8871) |
| miR-210 | 0.3579 (0.6268) | 0.8951 (1.2892) | 0.0054 | 0.6525 (0.5527 to 0.7523) |
| miR-301b | 0.2491 (0.2926) | 0.9524 (1.8623) | 0.0130 | 0.6115 (0.5201 to 0.7029) |

Abbreviations: PN, pulmonary nodules; SD, standard deviation; AUC, the area under receiver operating characteristic curve.

To determine the diagnostic values of the plasma miR-NAs, ROC and the AUCs were calculated by using the copy number of each miRNA in the UMMC cohort of 135 patients. The individual miRNAs exhibited AUC values of 0.57-0.82 in distinguishing malignant from benign PNs (Table 3). We used logistic regression models with constrained parameters as in LASSO based on ROC criterion to identify and optimize a panel of miRNA biomarkers. The three miRNAs, miRs-126, 210, and 205-5p are selected as the best biomarkers (all P<0.001). Combined use of the three miRNAs produced 0.87 AUC for distinguishing malignant from benign PNs. Furthermore, Pearson correlation analysis indicated that the estimated correlation among expression levels of the three miRNAs in plasma was low (All P>0.05), implying that the diagnostic values of the miRNAs were complementary to each other. Subsequently, combined use of the three miRNAs generated a sensitivity of 81.2% and a specificity of 86.4% (FIG. 1A). Moreover, including other miRNAs in the model did not improve the accuracy for the identification of malignant PNs. The logistic model had no statistically significant association with histological type and stage of the NSCLC, and patients' age, gender, ethnicity, and smoking history (All p>0.05).

Developing a Classifier by Integrating the Biomarkers and Radiographic Features of PNs for Identifying Malignant PNs Although showing promise, the 81.2% sensitivity and 86.4% specificity of the three miRNA biomarkers used together are not sufficient in the clinic for distinguishing malignant from benign PNs. We used univariate analysis to determine which of clinical and radiological variables were associated with malignant PNs in 135 patients of the UMMC cohort. History of cancer and smoking pack-years of the patients, the diameter, spiculation, and upper lobe location of the PNs were associated with malignant PNs (Table 4).

TABLE 4

Association of clinical and radiological variables with malignant PNs

| Variables | p-value |
|---|---|
| Age (year) | 0.1729 |
| Sex | 0.7388 |
| Race | 0.9648 |
| Current smoker | 0.2295 |
| Former smoker | 0.6548 |
| Smoking package-year | <0.0001 |
| Cancer history | <0.0001 |
| Nodule diameter on CT | <0.0001 |
| Nodule spiculation on CT | <0.0001 |
| Year after quit | 0.0126 |
| Upper lobe locations of PNs | 0.0065 |

Abbreviations: PN, pulmonary nodule.

We then used logistic regression models with constrained parameters as in LASSO based on ROC criterion to eliminate the large number of the parameters to construct a classifier including: miRs-205-5p and 126, and diameter of PN. The classifier had 0.95 AUC in distinguishing malignant from benign PNs (FIG. 1B). Adding other miRNAs and imaging/clinical variables in the classifier did not improve the performance for predicting malignant PNs. Furthermore, prediction models based on parameters of PN on CT images and clinical characteristics of smokers have been developed for predicting the probability of malignant PNs (Swensen S J, Silverstein M D, Ilstrup D M, et al. The probability of malignancy in solitary pulmonary nodules. Application to small radiologically indeterminate nodules. Arch Intern Med, 157: 849-55, 1997; Gould M K, Ananth L, Barnett P G. A clinical model to estimate the pretest probability of lung cancer in patients with solitary pulmonary nodules. Chest, 131: 383-8, 2007; Schultz E M, Sanders G D, Trotter P R, et al. Validation of two models to estimate the probability of malignancy in patients with solitary pulmonary nodules. Thorax, 63: 335-41, 2008; McWilliams A, Tammemagi M C, Mayo J R, et al. Probability of cancer in pulmonary nodules detected on first screening CT. N Engl J Med, 369: 910-9, 2013), of which, the Mayo Clinic model is a commonly used one. We applied the Mayo Clinic model (Swensen S J, Silverstein M D, Ilstrup D M, et al. The probability of malignancy in solitary pulmonary nodules. Application to small radiologically indeterminate nodules. Arch Intern Med, 157: 849-55, 1997) in the same set of 135 patients for predicting lung cancer by using the equation. The Mayo Clinic model produced an AUC of 0.82 (FIG. 1C), a similar value as shown in the previous reports (Swensen S J, Silverstein M D, Ilstrup D M, et al. The probability of malignancy in solitary pulmonary nodules. Application to small radiologically indeterminate nodules. Arch Intern Med, 157: 849-55, 1997; Gould M K, Ananth L, Barnett P G. A clinical model to estimate the pretest probability of lung cancer in patients with solitary pulmonary nodules. Chest, 131: 383-8, 2007; Schultz E M, Sanders G D, Trotter P R, et al. Validation of two models to estimate the probability of malignancy in patients with solitary pulmonary nodules. Thorax, 63: 335-41, 2008). The direct comparison showed that the classifier had a significantly higher AUC value (0.95) compared with the Mayo Clinic model (0.82) and the panel of three biomarkers (0.87) used alone (All P<0.05) in the same set of patients (FIG. 1A-C). As a result, our classifier yielded 89.9% sensitivity and 90.9% specificity for diagnosis of malignant PNs, which were also significantly higher compared with those of the Mayo Clinic model (75.4% sensitivity and 80.3% specificity) and the biomarkers (81.2% sensitivity and 86.4% specificity) (all P<0.05) (FIG. 1A-C). Moreover, the classifier did not exhibit statistical differences of sensitivity and specificity between histological types and stages of NSCLC (P>0.05).

Validating the Classifier for Differentiating Malignant from Benign PNs in Two Independent Cohorts of Patients with PNs The three miRNAs (miRs-126, 210, and 205-5p) were analyzed for the expression levels in plasma of both BVAMC and JPHTCM cohorts. The three miRNAs showed a similar change pattern in the two independent cohorts as in the UMMC cohort, providing additional evidence that the plasma miRNAs could be reproducibly measured. The classifier produced 0.94 AUC with a sensitivity of 88.9% and a specificity of 90.5% for diagnosis of malignant PNs in BVAMC cohort (Table 5). The classifier produced higher sensitivity and specificity than did the panel of the biomarkers (80.9% sensitivity and 85.7% specificity) and the Mayo Clinic model (74.6% sensitivity and 79.4% specificity) (All P<0.05) (Table 5). The classifier was further validated in an external set of 98 patients with PNs (the JPHTCM cohort) recruited in China for the diagnostic value in a blinded fashion. The classifier created an AUC of 0.94 with a sensitivity of 87.8% and a specificity of 89.8% for detection of malignant PNs. Furthermore, the classifier had higher sensitivity and specificity (87.8% sensitivity and 89.8% specificity) for detection of malignant PNs than did the panel of the biomarkers (81.6% sensitivity and 85.7% specificity) and the Mayo Clinic model (73.5% sensitivity and 75.5% specificity) (Table 5) (All P<0.05). Taken together, the results created from the extensive validations confirmed the potential of the classifier for estimating the probability of lung cancer among indeterminate PNs.

TABLE 5

Comparison of the classifier, panel of the three plasma miRNA biomarkers, and Mayo Clinic model for distinguishing malignant from benign PNs in two independent cohorts of patients*

| | BVAMC patients | | JPHTCM | |
|---|---|---|---|---|
| Approaches | Sensitivity (95% CI) | Specificity (95% CI) | Sensitivity (95% CI) | Specificity (95% CI) |
| The classifier | 88.89% (78.44% to 95.41%) | 90.48% (80.41% to 96.42%) | 87.76% (75.23% to 95.37%) | 89.80% (77.77% to 96.60%) |
| The biomarker panel | 80.95% (69.09% to 89.75%) | 85.71% (74.61% to 93.25%) | 81.63% (67.98% to 91.24%) | 85.71% (72.76% to 94.06%) |
| The Mayo Clinic model | 74.60% (62.06% to 84.73%) | 79.37% (67.30% to 88.53%) | 73.47% (58.92% to 85.05%) | 75.51% (61.13% to 86.66%) |

Abbreviations: BVAMC, Baltimore VA Medical Center patients; JPHTCM, Jiangsu Province Hospital of Traditional Chinese Medicine; CI, confidence interval.
*All P values < 0.05.

Example 2. A Plasma Long Non-Coding RNA Signature for Early Detection of Lung Cancer By using droplet digital PCR, we determined the diagnostic performance of 26 lung cancer-associated lncRNAs in plasma of a development cohort of 63 lung cancer patients and 33 cancer-free individuals, and a validation cohort of 39 lung cancer patients and 22 controls. In the development cohort, seven of the 26 lncRNAs were reliably measured in plasma. Two (SNHG1 and RMRP) displayed a considerably high plasma level in lung cancer patients vs. cancer-free controls (all P<0.001). Combined use of the plasma lncRNAs as a biomarker signature produced 84.13% sensitivity and 87.88% specificity for diagnosis of lung cancer, independent of stage and histological type of lung tumor, and patients' age and sex (all p>0.05). The diagnostic value of the plasma lncRNA signature for lung cancer early detection was confirmed in the validation cohort. The plasma lncRNA signature may provide a potential blood-based assay for diagnosing lung cancer at the early stage. Nevertheless, a prospective study is warranted to validate its clinical value.

Circulating cell-free lncRNAs biomarkers show promise as biomarkers for cancer diagnosis. However, unlike other ncRNA (e.g., microRNAs), lncRNAs have the lowest levels in plasma among several different RNA species (Schlosser, K., Hanson, J., Villeneuve, P. J., Dimitroulakos, J., McIntyre, L., Pilote, L., and Stewart, D. J. (2016) Sci Rep 6, 36596), presenting a major challenge for the development of cell-free lncRNA biomarkers. Schlosser et al recently demonstrated that expressions of lncRNAs were robustly detectable in tissues, however, undetectable or sporadically measurable in the matched plasma by using qRT-PCR, a routine platform used for nucleic acid detection[64]. Regular qPCR has some limitations in determining expression of ncRNAs: i), it is an indirect and labor-consuming approach. ii), it requires an internal control gene for normalization. Yet none of the investigated genes has been accepted as a standard control. iii), its sensitivity for a low copy number of genes is very low. Our current observations are consistent with Schlosser's finding (Schlosser, K., Hanson, J., Villeneuve, P. J., Dimitroulakos, J., McIntyre, L., Pilote, L., and Stewart, D. J. (2016) Sci Rep 6, 36596). Of the 26 lung cancer-associated lncRNAs, none is reliably measurable in plasma using qRT-PCR, when a CT of 35 is used as the cut off value. Therefore, conventional qPCR might not be an appropriate tool for the development of lncRNAs as circulating biomarkers, given that circulating lncRNAs in body fluids are present in low abundance. We have shown that ddPCR is a direct method for absolutely and quantitatively measuring ncRNAs (Ma, J., Li, N., Guarnera, M., and Jiang, F. (2013) Biomark Insights 8, 127-136; Li, N., Ma, J., Guarnera, M. A., Fang, H., Cai, L., and Jiang, F. (2014) J Cancer Res Clin Oncol 140, 145-150; Li, H., Jiang, Z., Leng, Q., Bai, F., Wang, J., Ding, X., Li, Y., Zhang, X., Fang, H., Yfantis, H. G., Xing, L., and Jiang, F. (2017) Oncotarget 8, 50704-50714), since it depends on limiting partition of the PCR volume, where a positive result of a large number of microreactions indicates the presence of a single molecule in a given reaction (Day, E., Dear, P. H., and McCaughan, F. (2013) Methods 59, 101-107). The number of positive reactions, together with Poisson's distribution produces a straight and high-confidence measurement of the original target concentration. Importantly, ddPCR does not require a reliance on rate-based measurements (CT values), endogenous controls, and calibration curves, and therefore overcome the obstacles linked to the regular qPCR in quantification of genes in plasma. Here we demonstrate that seven of the 26 lung cancer-associated lncRNAs that are not detectable by qRT-PCR are robustly measurable by ddPCR in plasma. Therefore, ddPCR may address the limitations of the qPCR in quantification of lncRNAs in plasma, and hence help develop cell-free cancer biomarkers.

The previous plasma lncRNA-based assays were mostly developed from the limited number of lung cancer-associated lncRNAs and only consisted of a single lncRNA gene (Liang, W., Lv, T., Shi, X., Liu, H., Zhu, Q., Zeng, J., Yang, W., Yin, J., and Song, Y. (2016) Medicine (Baltimore) 95, e4608; Tantai, J., Hu, D., Yang, Y., and Geng, J. (2015) Int J Clin Exp Pathol 8, 7887-7895; Li, N., Feng, X. B., Tan, Q., Luo, P., Jing, W., Zhu, M., Liang, C., Tu, J., and Ning, Y. (2017) Dis Markers 2017, 7439698; Li, N., Wang, Y., Liu, X., Luo, P., Jing, W., Zhu, M., and Tu, J. (2017) Technol Cancer Res Treat, 1533034617723754; Wan, L., Zhang, L., Fan, K., and Wang, J. J. (2017) Onco Targets Ther 10, 5695-5702; Tan, Q., Zuo, J., Qiu, S., Yu, Y., Zhou, H., Li, N., Wang, H., Liang, C., Yu, M., and Tu, J. (2017) Int J Oncol 50, 1729-1738; Zhu, Q., Lv, T., Wu, Y., Shi, X., Liu, H., and Song, Y. (2017) J Cell Mol Med 21, 2184-2198; Zhu, H., Zhang, L., Yan, S., Li, W., Cui, J., Zhu, M., Xia, N., Yang, Y., Yuan, J., Chen, X., Luo, J., Chen, R., Xing, R., Lu, Y., and Wu, N. (2017) Oncotarget 8, 7867-7877; Wang, H. M., Lu, J. H., Chen, W. Y., and Gu, A. Q. (2015) Int J Clin Exp Med 8, 11824-11830).

Since lung tumor is a heterogeneous group of neoplasms and develops from a multitude of molecular changes, a single lncRNA-based assay may not achieve the performance required to move forward for clinically detecting lung cancer. The development of a panel of multiple biomarkers by integrating analysis of multifaceted and diverse lncRNAs would provide a synergistic test for lung cancer diagnosis. By searching published data, we found 21 lncRNAs whose malfunction was well characterized in lung tumorigenesis (Li, M., Qiu, M., Xu, Y., Mao, Q., Wang, J., Dong, G., Xia, W., Yin, R., and Xu, L. (2015) Tumour Biol 36, 9969-9978; Wei, M. M., Zhou, Y. C., Wen, Z. S., Zhou, B., Huang, Y. C., Wang, G. Z., Zhao, X. C., Pan, H. L., Qu, L. W., Zhang, J., Zhang, C., Cheng, X., and Zhou, G. B. (2016) Oncotarget 7, 59556-59571; Shen, L., Chen, L., Wang, Y., Jiang, X., Xia, H., and Zhuang, Z. (2015) J Neurooncol 121, 101-108; Loewen, G., Jayawickramarajah, J., Zhuo, Y., and Shan, B. (2014) J Hematol Oncol 7, 90; Li, P., Li, J., Yang, R., Zhang, F., Wang, H., Chu, H., Lu, Y., Dun, S., Wang, Y., Zang, W., Du, Y., Chen, X., Zhao, G., and Zhang, G. (2015) Diagn Pathol 10, 63; Yang, Y. R., Zang, S. Z., Zhong, C. L., Li, Y. X., Zhao, S. S., and Feng, X. J. (2014) Int J Clin Exp Pathol 7, 6929-6935; Whiteside, E. J., Seim, I., Pauli, J. P., O'Keeffe, A. J., Thomas, P. B., Carter, S. L., Walpole, C. M., Fung, J. N., Josh, P., Herington, A. C., and Chopin, L. K. (2013) Int J Oncol 43, 566-574; Hu, T., and Lu, Y. R. (2015) Cancer Cell Int 15, 36; Li, J., Li, P., Zhao, W., Yang, R., Chen, S., Bai, Y., Dun, S., Chen, X., Du, Y., Wang, Y., Zang, W., Zhao, G., and Zhang, G. (2015) Cancer Cell Int 15, 48; Zeng, Z., Bo, H., Gong, Z., Lian, Y., Li, X., Zhang, W., Deng, H., Zhou, M., Peng, S., Li, G., and Xiong, W. (2016) Tumour Biol 37, 729-737; Hou, Z., Zhao, W., Zhou, J., Shen, L., Zhan, P., Xu, C., Chang, C., Bi, H., Zou, J., Yao, X., Huang, R., Yu, L., and Yan, J. (2014) Int J Biochem Cell Biol 53, 380-388; Luo, J., Tang, L., Zhang, J., Ni, J., Zhang, H. P., Zhang, L., Xu, J. F., and Zheng, D. (2014) Tumour Biol 35, 11541-11549; Luo, H., Sun, Y., Wei, G., Luo, J., Yang, X., Liu, W., Guo, M., and Chen, R. (2015) Biochemistry 54, 2895-2902; Wu, Y., Liu, H., Shi, X., Yao, Y., Yang, W., and Song, Y. (2015) Oncotarget 6, 9160-9172; Qiu, M., Xu, Y., Yang, X., Wang, J., Hu, J., Xu, L., and Yin, R. (2014) Tumour Biol 35, 5375-5380; Qiu, M., Xu, Y., Wang, J., Zhang, E., Sun, M., Zheng, Y., Li, M., Xia, W., Feng, D., Yin, R., and Xu, L. (2015) Cell Death Dis 6, e1858; Zhang, L., Zhou, X. F., Pan, G. F., and Zhao, J. P. (2014) Biomed Pharmacother 68, 401-407; Nie, F. Q., Sun, M., Yang, J. S., Xie, M., Xu, T. P., Xia, R., Liu, Y. W., Liu, X. H., Zhang, E. B., Lu, K. H., and Shu, Y. Q. (2015) Mol Cancer Ther 14, 268-277; Yang, R., Li, P., Zhang, G., Lu, C., Wang, H., and Zhao, G. (2017) Cell Physiol Biochem 42, 126-136; Sang, H., Liu, H., Xiong, P., and Zhu, M. (2015) Tumour Biol 36, 4027-4037; Shi, X., Sun, M., Liu, H., Yao, Y., Kong, R., Chen, F., and Song, Y. (2015) Mol Carcinog 54 Suppl 1, E1-E12; Han, L., Kong, R., Yin, D. D., Zhang, E. B., Xu, T. P., De, W., and Shu, Y. Q. (2013) Med Oncol 30, 694; Han, L., Zhang, E. B., Yin, D. D., Kong, R., Xu, T. P., Chen, W. M., Xia, R., Shu, Y. Q., and De, W. (2015) Cell Death Dis 6, e1665; Xie, X., Liu, H. T., Mei, J., Ding, F. B., Xiao, H. B., Hu, F. Q., Hu, R., and Wang, M. S. (2014) Int J Clin Exp Pathol 7, 8881-8886; Liu, J., Wan, L., Lu, K., Sun, M., Pan, X., Zhang, P., Lu, B., Liu, G., and Wang, Z. (2015) PLoS One 10, e0114586; Sun, M., Liu, X. H., Wang, K. M., Nie, F. Q., Kong, R., Yang, J. S., Xia, R., Xu, T. P., Jin, F. Y., Liu, Z. J., Chen, J. F., Zhang, E. B., De, W., and Wang, Z. X. (2014) Mol Cancer 13, 68; Yang, Y., Li, H., Hou, S., Hu, B., Liu, J., and Wang, J. (2013) PLoS One 8, e65309).

Furthermore, by systematically and comprehensively define ncRNA changes of NSCLC in surgical lung tumor tissues using whole-transcriptome NGS (Ma, J., Mannoor, K., Gao, L., Tan, A., Guarnera, M. A., Zhan, M., Shetty, A., Stass, S. A., Xing, L., and Jiang, F. (2014) Mol Oncol 8, 1208-1219; Gao, L., Ma, J., Mannoor, K., Guarnera, M. A., Shetty, A., Zhan, M., Xing, L., Stass, S. A., and Jiang, F. (2015) Int J Cancer 136, E623-629), we recently identified additional five lung cancer-associated lncRNAs (Ma, J., Mannoor, K., Gao, L., Tan, A., Guarnera, M. A., Zhan, M., Shetty, A., Stass, S. A., Xing, L., and Jiang, F. (2014) Mol Oncol 8, 1208-1219; Gao, L., Ma, J., Mannoor, K., Guarnera, M. A., Shetty, A., Zhan, M., Xing, L., Stass, S. A., and Jiang, F. (2014) Int J Cancer).

Both the published and our NGS-defied lncRNAs of lung tumors may provide a comprehensive set of high-quality biomarker candidates for lung cancer. From the 26 lncRNAs, our present study identified and optimized a plasma signature consisting of two lncRNAs that created a higher diagnostic value for lung cancer detection than did individual lncRNAs used alone (Liang, W., Lv, T., Shi, X., Liu, H., Zhu, Q., Zeng, J., Yang, W., Yin, J., and Song, Y. (2016) Medicine (Baltimore) 95, e4608; Tantai, J., Hu, D., Yang, Y., and Geng, J. (2015) Int J Clin Exp Pathol 8, 7887-7895; Li, N., Feng, X. B., Tan, Q., Luo, P., Jing, W., Zhu, M., Liang, C., Tu, J., and Ning, Y. (2017) Dis Markers 2017, 7439698; Li, N., Wang, Y., Liu, X., Luo, P., Jing, W., Zhu, M., and Tu, J. (2017) Technol Cancer Res Treat, 1533034617723754; Wan, L., Zhang, L., Fan, K., and Wang, J. J. (2017) Onco Targets Ther 10, 5695-5702; Tan, Q., Zuo, J., Qiu, S., Yu, Y., Zhou, H., Li, N., Wang, H., Liang, C., Yu, M., and Tu, J. (2017) Int J Oncol 50, 1729-1738; Zhu, Q., Lv, T., Wu, Y., Shi, X., Liu, H., and Song, Y. (2017) J Cell Mol Med 21, 2184-2198; Zhu, H., Zhang, L., Yan, S., Li, W., Cui, J., Zhu, M., Xia, N., Yang, Y., Yuan, J., Chen, X., Luo, J., Chen, R., Xing, R., Lu, Y., and Wu, N. (2017) Oncotarget 8, 7867-7877; Wang, H. M., Lu, J. H., Chen, W. Y., and Gu, A. Q. (2015) Int J Clin Exp Med 8, 11824-11830).

In addition, the diagnostic performance of the biomarkers was further blindly validated in a different cohort, suggesting that the plasma signature might be a robust assay for lung cancer diagnosis. Moreover, the performance of this plasma lncRNA signature for lung cancer diagnosis was independent of tumor stage and histology. This might be an important characteristic if the plasma lncRNA signature is employed for identifying early stage lung cancer.

The two lncRNAs (SNHG1 and RMRP) have diverse and important functions in lung tumorigenesis through regulating different molecular pathways. Elevated expression of SNHG1 was frequently observed in lung cancer tissues and significantly correlated with larger tumor size, advanced stage, lymph node metastasis and poor overall survival of the patients (Cui, Y., Zhang, F., Zhu, C., Geng, L., Tian, T., and Liu, H. (2017) Oncotarget 8, 17785-17794). Furthermore, SNHG1 could promote NSCLC progression of lung cancer via miR-101-3p/SOX9/Wnt/β-catenin regulatory network and miR-145-5p/MTDH axis (Lu, Q., Shan, S., Li, Y., Zhu, D., Jin, W., and Ren, T. (2018) FASEB J, fj201701237RR; Cui, Y., Zhang, F., Zhu, C., Geng, L., Tian, T., and Liu, H. (2017) Oncotarget 8, 17785-17794). In addition, SNHG1 plays an oncogenic role in lung squamous cell carcinoma through ZEB1 signaling pathway by inhibiting TAp63 (Zhang, H. Y., Yang, W., Zheng, F. S., Wang, Y. B., and Lu, J. B. (2017) Biomed Pharmacother 90, 650-658). RMRP is best known for being a component of the nuclear RNase MRP complex, which participates in the processing of ribosomal RNA to generate the short mature 5.8S rRNA (Schmitt, M. E., and Clayton, D. A. (1993) Mol Cell Biol 13, 7935-7941) and cleaves B-cyclin mRNA, lowering B-cyclin levels during mitosis (Noh, J. H., Kim, K. M., Abdelmohsen, K., Yoon, J. H., Panda, A. C., Munk, R., Kim, J., Curtis, J., Moad, C. A., Wohler, C. M., Indig, F. E., de Paula, W., Dudekula, D. B., De, S., Piao, Y., Yang, X., Martindale, J. L., de Cabo, R., and Gorospe, M. (2016) Genes Dev 30, 1224-1239). In addition, RMRP interacts with telomerase to form a complex with RNA-dependent RNA polymerase activity capable of synthesizing dsRNA precursors processed by DICER1 into siRNAs (Maida, Y., Yasukawa, M., Furuuchi, M., Lassmann, T., Possemato, R., Okamoto, N., Kasim, V., Hayashizaki, Y., Hahn, W. C., and Masutomi, K. (2009) Nature 461, 230-235). Moreover, RMRP is important for mitochondrial DNA replication and RNA processing (Chang, D. D., and Clayton, D. A. (1987) Science 235, 1178-1184). Upregulation of RMRP is found in lung adenocarcinoma tissues (Meng, Q., Ren, M., Li, Y., and Song, X. (2016) PLoS One 11, e0164845). RMRP might act as an oncogenic lncRNA to promote the expression of KRAS, FMNL2 and SOX9 by inhibiting miR-206 expression in lung cancer (Meng, Q., Ren, M., Li, Y., and Song, X. (2016) PLoS One 11, e0164845). Our current study extends the previous findings by developing them as a biomarker signature that might be clinically useful in the early detection of lung cancer.

Materials and Methods

Patients and Clinical Specimens

This study was approved by the Institutional Review Boards of University of Maryland Baltimore and Veterans Affairs Maryland Health Care System. We recruited lung cancer patients and cancer-free smokers by using the inclusion and/or exclusion criteria recommended by U.S. Preventive Services Task Force for lung cancer screening in heavy smokers (Humphrey, L. L., Deffebach, M., Pappas, M., Baumann, C., Artis, K., Mitchell, J. P., Zakher, B., Fu, R., and Slatore, C. G. (2013) Ann Intern Med 159, 411-420). We collected blood in BD Vacutainer spray-coated K2EDTA Tubes (BD, Franklin Lakes, N.J.) and prepared plasma using the standard operating protocols developed by The NCI-Early Detection Research Network (Marks, J. R., Anderson, K. S., Engstrom, P., Godwin, A. K., Esserman, L. J., Longton, G., Iversen, E. S., Mathew, A., Patriotis, C., and Pepe, M. S. (2015) Cancer Epidemiol Biomarkers Prev 24, 435-

441; Tuck, M. K., Chan, D. W., Chia, D., Godwin, A. K., Grizzle, W. E., Krueger, K. E., Rom, W., Sanda, M., Sorbara, L., Stass, S., Wang, W., and Brenner, D. E. (2009) J Proteome Res 8, 113-117). The specimens were processed within 2 hours of collection by centrifugation at 1,300×g for 10 minutes at 4° C. A total of 102 NSCLC patients and 55 cancer-free smokers were recruited. Among the cancer patients, 24 patients were female and 78 were male. Twenty-three had stage I NSCLC, 18 with stage II, 28 with stage III, 28 with stage IV, and 5 with unknown stage. Of the cancer-free smokers, 14 patients were female and 41 were male. There were no significant differences of age, gender and smoking status between the NSCLC patients and cancer-free smokers. The cases and controls were randomly grouped into two cohorts: a development cohort and a validation cohort. The development cohort consisted of 63 lung cancer patients and 33 cancer-free smokers, while the validation cohort comprised 39 lung cancer patients and 22 cancer-free smokers. The demographic and clinical variables of the two cohorts are shown in Tables 6-7.

RNA Isolation and Quantitative Reverse Transcriptase PCR (qRT-PCR)

RNA was extracted from the specimens by using Trizol LS reagent (Invitrogen Carlsbad, Calif.) and RNeasy Mini Kit (Qiagen, Hilden, Germany) (Ma, J., Jemal, A., and Smith, R. (2013) Cancer 119, 3420-3421; Shen, J., Liu, Z., Todd, N. W., Zhang, H., Liao, J., Yu, L., Guarnera, M. A., Li, R., Cai, L., Zhan, M., and Jiang, F. (2011) BMC Cancer 11, 374; Shen, J., Todd, N. W., Zhang, H., Yu, L., Lingxiao, X., Mei, Y., Guarnera, M., Liao, J., Chou, A., Lu, C. L., Jiang, Z., Fang, H., Katz, R. L., and Jiang, F. (2011) Lab Invest 91, 579-587). RT was carried out to generate cDNA by using a RT Kit (Applied Biosystems, Foster City, Calif.) as described in our published works (Ma, J., Jemal, A., and Smith, R. (2013) Cancer 119, 3420-3421; Shen, J., Liu, Z., Todd, N. W., Zhang, H., Liao, J., Yu, L., Guarnera, M. A., Li, R., Cai, L., Zhan, M., and Jiang, F. (2011) BMC Cancer 11, 374; Shen, J., Todd, N. W., Zhang, H., Yu, L., Lingxiao, X., Mei, Y., Guarnera, M., Liao, J., Chou, A., Lu, C. L., Jiang, Z., Fang, H., Katz, R. L., and Jiang, F. (2011) Lab Invest 91, 579-587). PCR was performed to measure expressions of target genes by using a PCR kit (Applied Biosystems) on a Bio-Red IQ5 Muilt-color RT-PCR Detection System (Bio-Red, Hercules, Calif.). Expression levels of the genes were determined using comparative cycle threshold (CT) method with miR-1228 as an internal control. The targeted genes with CT values>35 were considered to be below the detection level of qRT-PCR (Guthrie, J. L., Seah, C., Brown, S., Tang, P., Jamieson, F., and Drews, S. J. (2008) J Clin Microbiol 46, 3798-3799).

Droplet Digital PCR ddPCR for analysis of expression level of the genes was performed as described in our previous work (Li, N., Ma, J., Guarnera, M. A., Fang, H., Cai, L., and Jiang, F. (2014) J Cancer Res Clin Oncol 140, 145-150; Ma, J., Li, N., Guarnera, M., and Jiang, F. (2013) Biomark Insights 8, 127-136). Briefly, TaqMan™ reaction mix (Applied Biosystems) containing sample cDNA was partitioned into aqueous droplets in oil via the QX100 Droplet Generator (Bio-Rad), and then transferred to a 96-well PCR plate. A two-step thermocycling protocol (95° C.×10 min; 40 cycles of [94° C.×30 s, 60° C.×60 s], 98° C.×10 min) was undertaken in a Bio-Rad C1000 (Bio-Rad). The PCR plate was loaded on Droplet Reader (Bio-Rad), by which copy number of each gene per µl PCR reaction was directly determined. We used QuantaSoft 1.7.4 analysis software (Bio-Rad) and Poisson statistics to compute droplet concentrations (copies/µL). Only genes that had at least 10,000 droplets were considered to be robustly detectable by ddPCR in plasma and subsequently underwent further analysis (Ma, J., Li, N., Guarnera, M., and Jiang, F. (2013) Biomark Insights 8, 127-136; Li, N., Ma, J., Guarnera, M. A., Fang, H., Cai, L., and Jiang, F. (2014) J Cancer Res Clin Oncol 140, 145-150). All assays were done in triplicates, and one no-template control and two interplate controls were carried along in each experiment.

Statistical Analysis

Pearson's correlation analysis was applied to assess relationship between gene expressions and demographic and clinical characteristics of the lung cancer patients and control individuals. The area under receiver operating characteristic (ROC) curve (AUC) analyses were used to determine sensitivity, specificity, and corresponding cut-off value of each gene (Dodd, L. E., and Pepe, M. S. (2003) Biometrics 59, 614-623). All P values shown were two sided, and a P value of <0.05 was considered statistically significant.

Results

Developing a Plasma lncRNA Signature for Lung Cancer Early Detection

We first measured expression levels of the 26 lncRNAs in plasma by using qRT-PCR in a discovery cohort of 63 cases and 33 controls. The lncRNAs had a CT value of ≥35 in 75% plasma samples. However, the internal control gene, miR-1228, stably displayed a CT value of 20-22 across the plasma samples. The results suggested that the amplification curves for the lncRNAs were not reliably generated, and their expression levels in plasma were too low to be detectable by qRT-PCR. We have proven that ddPCR is a direct method for absolutely and quantitatively measuring ncRNAs with a higher sensitivity compared with qRT-PCR (Ma, J., Li, N., Guarnera, M., and Jiang, F. (2013) Biomark Insights 8, 127-136; Li, N., Ma, J., Guarnera, M. A., Fang, H., Cai, L., and Jiang, F. (2014) J Cancer Res Clin Oncol 140, 145-150; Li, H., Jiang, Z., Leng, Q., Bai, F., Wang, J., Ding, X., Li, Y., Zhang, X., Fang, H., Yfantis, H. G., Xing, L., and Jiang, F. (2017) Oncotarget 8, 50704-50714). Therefore, we used ddPCR to determine expression level of the lncRNAs in the plasma samples. Seven (26.9%) of the 26 lncRNAs could generated at least 10,000 droplets in each well of the plasma samples. Therefore, the seven lncRNAs could be successfully "read" by ddPCR for the absolute quantification in the plasma samples. The seven genes are SNHG1, MALAT1, HOTAIR, H19, MEG3, MEG8, and RMRP.

TABLE 6

Characteristics of NSCLC patients and cancer-free smokers in a development cohort

| | NSCLC cases (n = 63) | Controls (n = 33) | P-value |
|---|---|---|---|
| Age | 67.93 (SD9.16) | 63.79 (SD 16.12) | 0.18 |
| Sex | | | 0.36 |
| Female | 15 | 8 | |
| Male | 48 | 25 | |
| Smoking pack-years (median) | 32.1 | 31.76 | 0.19 |
| Stage | | | |
| Stage I | 14 | | |
| Stage II | 10 | | |
| Stage III | 17 | | |
| Stage IV | 18 | | |
| Unknown | 4 | | |
| Histological type | | | |

TABLE 7

Characteristics of NSCLC patients and cancer-free smokers in a validation cohort

|  | NSCLC cases (n = 39) | Controls (n = 22) | P-value |
|---|---|---|---|
| Age | 66.58 (SD 9.93) | 63.68 (SD 13.27) | 0.25 |
| Sex |  |  | 0.45 |
| Female | 9 | 6 |  |
| Male | 30 | 16 |  |
| Smoking pack-years (median) | 33.39 | 29.64 | 0.26 |
| Stage |  |  |  |
| Stage I | 9 |  |  |
| Stage II | 8 |  |  |
| Stage III | 11 |  |  |
| Stage IV | 10 |  |  |
| Unknown | 1 |  |  |
| Histological type |  |  |  |
| Adenocarcinoma | 22 |  |  |
| Squamous cell carcinoma | 17 |  |  |

Abbreviations: NSCLC, non-small cell lung cancer.

Figure 2:
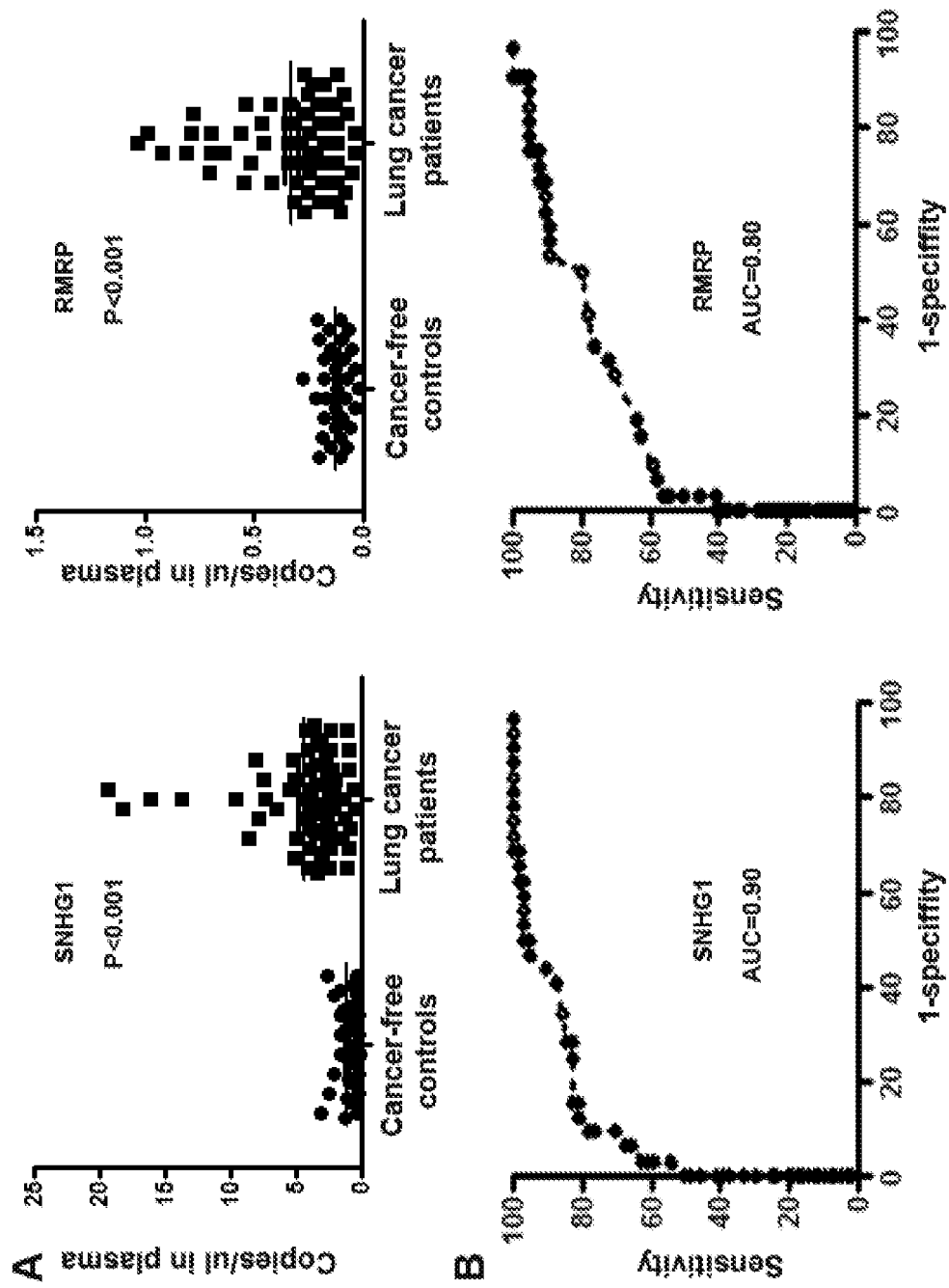
FIG. 2. Expression levels of SNHG1 and RMRP in plasma samples of 63 lung cancer patients and 33 cancer-free controls. (A), SNHG1 and RMRP displayed a higher plasma level in lung cancer patients vs. cancer-free controls (all p<0.001). (B), the receiver operating characteristic (ROC) curves of SNHG1 and RMRP produced an area under the ROC curve (AUC) of 0.90 and 0.80, respectively, in diagnosis of lung cancer.

Of the seven genes, SNHG1 and RMRP had an elevated plasma level in lung cancer patients vs. cancer-free controls (All p<0.05) (FIG. 2A), being consistent with those in primary lung tumor tissues (Cui, Y., Zhang, F., Zhu, C., Geng, L., Tian, T., and Liu, H. (2017) Oncotarget 8, 17785-17794; Meng, Q., Ren, M., Li, Y., and Song, X. (2016) PLoS One 11, e0164845). Therefore, the level of the two lncRNAs in plasma might reflect those in the tumors of the lung cancer patients. However, other five lncRNAs did not exhibit a different plasma level in lung cancer cases vs. controls (All p>0.05). Furthermore, SNHG1 and RMRP exhibited AUC values of 0.90 and 0.80, respectively, in distinguishing NSCLC patients from the healthy individuals (FIG. 2B). Using Youden's index (Schisterman, E. F., Perkins, N. J., Liu, A., and Bondell, H. (2005) Epidemiology 16, 73-81), we set up optimal cutoff for the two genes at 1.11 and 0.12, respectively. As a result, the use of the individual genes alone produced 61.00-78.78% sensitivities and 87.88-90.91% (Table 8). Combined use of the two genes based on at least one positive result in either SNHG1 or RMRP produced the highest classification accuracy (85.42%) compared to any one used alone (all p<0.05) (Table 8). The two genes used in combination produced a sensitivity of 84.13% and a specificity of 87.88% for diagnosis of lung cancer, thus considerably improving the detection rate by a single gene with only a 2% decline in specificity (Table 8). Furthermore, the estimated correlation determined by Pearson's correlation analysis among levels of the two lncRNAs was very low ($R2=0.011$, $p=0.53$), further supporting that the combined analysis of the two genes outperformed a single one. In addition, combined analysis of the 2 plasma biomarkers did not show special association with stage and histological type of lung cancer, and patients' age, gender, and smoking status (All P>0.05).

TABLE 8

Diagnostic performance of one-gene and vs. a plasma lncRNA signature for lung cancer diagnosis in a development cohort.

|  | Accuracy | Sensitivity (95% CI) | Specificity (95% CI) |
|---|---|---|---|
| SNHG1 | 81.25% (72.00% to 88.49%) | 77.78% (65.54% to 87.28%) | 87.88% (71.80% to 96.60%) |
| RMRP | 71.88% (61.78% to 80.58%) | 61.90% (48.80% to 73.85%) | 90.91% (75.67% to 98.08%) |
| A plasma lncRNA signature | 85.42% (76.74% to 91.79%) | 84.13% (72.74% to 92.12%) | 87.50% (71.80% to 96.60%) |

Abbreviations: CI, confidence interval.

Validating the Plasma lncRNA Marker Signature in an Independent Set of Lung Cancer Patients and Controls To evaluate the diagnostic performance of the biomarker signature, the lncRNAs (SNHG1 and RMRP) were assessed by using ddPCR in plasma of additional 39 NSCLC patients and 22 healthy controls. The two genes used in combination could differentiate the NSCLC patients from healthy controls with 82.05% sensitivity and 83.36% specificity (Table 9).

TABLE 9

Diagnostic performance of one-gene and vs. a plasma lncRNA signature for lung cancer diagnosis in a validation set

|  | Accuracy | Sensitivity (95% CI) | Specificity (95% CI) |
|---|---|---|---|
| SNHG1 | 80.33% (68.16% to 89.40%) | 76.92% (60.67% to 88.87) | 86.36% (65.09% to 97.09%) |
| RMRP | 72.13% (59.17% to 82.85%) | 61.54% (44.62% to 76.64%) | 90.91% (70.84% to 98.88%) |

TABLE 9-continued

Diagnostic performance of one-gene and vs. a plasma lncRNA
signature for lung cancer diagnosis in a validation set

|  | Accuracy | Sensitivity (95% CI) | Specificity (95% CI) |
| --- | --- | --- | --- |
| A plasma lncRNA signature | 83.62% (71.91% to 91.85%) | 82.05% (66.47% to 92.46%) | 86.36% (65.09% to 97.09%) |

Abbreviations: CI, confidence interval.

Furthermore, no statistically significant difference was found in the sensitivity and specificity of the biomarker signature for stages and histological types of NSCLC (All $p>0.05$). Moreover, there was no association of expressions of the two genes with the age, gender, or smoking status of the lung cancer patients and normal individuals (All $p>0.05$). Taken together, the results confirm the potential of using the two lncRNAs as a plasma biomarker signature for the early detection of lung cancer.

Example 3. Fucosylation Genes as Circulating Biomarkers for Lung Cancer

Here we investigated whether transcriptional levels of genes coding the FUTs in plasma could provide cell-free circulating biomarkers for lung cancer. mRNA expression of all 13 Futs (Fut1-11, Pofut1, and Pofut2) was evaluated in lung tumor tissues and the matched noncancerous lung tissues and plasma of 64 lung cancer patients and 32 cancer-free individuals by PCR assay. The developed plasma Fut biomarkers were validated in an independent cohort of 40 lung cancer patients and 20 controls for their diagnostic performance.

Four of the 13 Futs showed a different transcriptional level in 48 lung tumor tissues compared with the matched nonconscious tissues (All <0.05). Two (Fut8, and Pofut1) of the four Futs had a higher plasma level in lung cancer patients compared with control subjects, and consistent with that in lung tissue specimens. Combined analysis of the two Futs produced 81% sensitivity and 86% specificity for diagnosis of lung cancer, and was independent of stage and histology of lung tumors. The diagnostic performance of the two plasma biomarkers was successfully validated in the different cohort of lung cancer patients and control individuals. The fucosylation genes may provide new circulating biomarkers for the early detection of lung cancer.

In this present study, we have for the first time demonstrated that mRNA expression of Futs could provide cell-free circulating biomarkers for lung cancer. Furthermore, using ddPCR assay, a sensitive and robust technique, we successfully developed 2 Futs as small panel biomarkers for effective diagnosis of lung cancer. In addition, the diagnostic performance is independent of stage and histological type of the NSCLC, and age and gender of subjects. Therefore, the plasma biomarkers have an important characteristic if it is employed for more precisely and easily identifying early stage lung cancer.

Chen et al. showed that Fut8 was up-regulated in lung cancer and tissues (Chen C Y, Jan Y H, Juan Y H, Yang C J, Huang M S, Yu C J, Yang P C, Hsiao M, Hsu T L, Wong C H: Fucosyltransferase 8 as a functional regulator of nonsmall cell lung cancer. Proc Natl Acad Sci USA 2013, 110(2):630-635). A high protein expression of FUT8 was correlated with tumor metastasis, disease recurrence, and poor survival in patients with NSCLC (Honma R, Kinoshita I, Miyoshi E, Tomaru U, Matsuno Y, Shimizu Y, Takeuchi S, Kobayashi Y, Kaga K, Taniguchi N et al: Expression of fucosyltransferase 8 is associated with an unfavorable clinical outcome in non-small cell lung cancers. Oncology 2015, 88(5):298-308; Chen C Y, Jan Y H, Juan Y H, Yang C J, Huang M S, Yu C J, Yang P C, Hsiao M, Hsu T L, Wong C H: Fucosyltransferase 8 as a functional regulator of nonsmall cell lung cancer. Proc Natl Acad Sci USA 2013, 110(2):630-635). Downregulation of Fut8 significantly inhibited the malignant behaviors of lung cancer cells. Fut8 could globally modify surface antigens, receptors, and adhesion molecules (Chen C Y, Jan Y H, Juan Y H, Yang C J, Huang M S, Yu C J, Yang P C, Hsiao M, Hsu T L, Wong C H: Fucosyltransferase 8 as a functional regulator of nonsmall cell lung cancer. Proc Natl Acad Sci USA 2013, 110(2):630-635). Dysregulation of Fut8 was involved in the regulation of dozens of genes associated with the malignancy through multiple mechanisms (Chen C Y, Jan Y H, Juan Y H, Yang C J, Huang M S, Yu C J, Yang P C, Hsiao M, Hsu T L, Wong C H: Fucosyltransferase 8 as a functional regulator of nonsmall cell lung cancer. Proc Natl Acad Sci USA 2013, 110(2):630-635). The observations in the present study provide further evidence that dysregulation of FUT8 has important role in lung tumorigenesis. Importantly, we demonstrate that a high mRNA expression level of Fut8 in plasma may provide useful biomarker for lung cancer early detection. POFUT1 is an important 0-glycosyltransferase and has an essential role for extracellular Fringe to function (Stahl M, Uemura K, Ge C, Shi S, Tashima Y, Stanley P: Roles of Pofut1 and O-fucose in mammalian Notch signaling. J Biol Chem 2008, 283(20):13638-13651; Loriol C, Audfray A, Dupuy F, Germot A, Maftah A: The two N-glycans present on bovine Pofut1 are differently involved in its solubility and activity. FEBS J 2007, 274(5):1202-1211). POFUT1 can active Notch1 in breast cancer (Wan G, Tian L, Yu Y, Li F, Wang X, Li C, Deng S, Yu X, Cai X, Zuo Z et al: Overexpression of Pofut1 and activated Notch1 may be associated with poor prognosis in breast cancer. Biochem Biophys Res Commun 2017, 491(1):104-111). Analysis of POFUT1 may have diagnostic or prognostic value in the patients with cancers (Wan G, Tian L, Yu Y, Li F, Wang X, Li C, Deng S, Yu X, Cai X, Zuo Z et al: Overexpression of Pofut1 and activated Notch1 may be associated with poor prognosis in breast cancer. Biochem Biophys Res Commun 2017, 491(1):104-111; Dong S, Wang Z, Huang B, Zhang J, Ge Y, Fan Q: Bioinformatics insight into glycosyltransferase gene expression in gastric cancer: POFUT1 is a potential biomarker. Biochem Biophys Res Commun 2017, 483(1): 171-177). Ma et al. found that POFUT1 overexpression could prompt the binding of Notch ligand Dll1 to Notch1 receptor, and thus activated Notch1 signaling pathway in hepatocellular carcinoma cells (Ma L, Dong P, Liu L, Gao Q, Duan M, Zhang S, Chen S, Xue R, Wang X: Overexpression of protein O-fucosyltransferase 1 accelerates hepatocellular carcinoma progression via the Notch signaling pathway. Biochem Biophys Res Commun 2016, 473(2):503-510). Here we report an elevated mRNA level of Pofut1 in both lung tumor tissues and plasm specimens of lung cancer patients, suggesting that the gene play an important biological function in lung carcinogenesis. Nevertheless, the possible biological role of aberrant expression of Fut8 and Pofut1 in lung cancer development and progression is warranted to be investigated.

Materials and Methods

Patients and Clinical Specimens

This study was approved by the Institutional Review Boards of University of Maryland Baltimore and Veterans Affairs Maryland Health Care System. Surgically resected tissue specimens were obtained from 46 lung cancer patients who had either a lobectomy or a pneumonectomy. Tumor tissues were intraoperatively dissected from the surrounding lung parenchyma. The paired normal lung tissues were also obtained from the same patients at an area distant from their tumors. Serial cryostat sections from the specimens were prepared and used to confirm the diagnosis based on the WHO classification of tumors of the lung 10. All 48 cases were diagnosed with histologically confirmed stage I NSCLC, including 25 AC and 23 SCC.

To collect plasma samples, we recruited lung cancer patients and cancer-free smokers by using the inclusion and/or exclusion criteria recommended by U.S. Preventive Services Task Force for lung cancer screening in heavy smokers (Humphrey L L, Deffebach M, Pappas M, Baumann C, Artis K, Mitchell J P, Zakher B, Fu R, Slatore C G: Screening for lung cancer with low-dose computed tomography: a systematic review to update the US Preventive services task force recommendation. Ann Intern Med 2013, 159(6):411-420). We collected blood in BD Vacutainer spray-coated K2EDTA Tubes (BD, Franklin Lakes, N.J.) and prepared plasma using the standard operating protocols (SOPs) developed by The NCI-Early Detection Research Network (EDRN) (Marks J R, Anderson K S, Engstrom P, Godwin A K, Esserman L J, Longton G, Iversen E S, Mathew A, Patriotis C, Pepe M S: Construction and analysis of the NCI-EDRN breast cancer reference set for circulating markers of disease. Cancer Epidemiol Biomarkers Prev 2015, 24(2):435-441; Tuck M K, Chan D W, Chia D, Godwin A K, Grizzle W E, Krueger K E, Rom W, Sanda M, Sorbara L, Stass S et al: Standard operating procedures for serum and plasma collection: early detection research network consensus statement standard operating procedure integration working group. J Proteome Res 2009, 8(1):113-117). The specimens were processed within 2 hours of collection by centrifugation at 1,300×g for 10 minutes at 4° C. A total of 104 NSCLC patients and 52 cancer-free smokers were recruited. Among the cancer patients, 26 patients were female and 78 were male. Twenty-five had stage I NSCLC, 17 with stage II, 28 with stage III, 29 with stage IV, and 5 with unknown stage. Of the cancer-free smokers, 13 patients were female and 39 were male. There were no significant differences of age, gender and smoking status between the NSCLC patients and cancer-free smokers. In this study, the cases and controls were randomly grouped into two cohorts: a development cohort and a validation cohort. The development cohort consisted of 64 lung cancer patients and 32 cancer-free smokers, while the validation cohort comprised 40 lung cancer patients and 20 cancer-free smokers. The demographic and clinical variables of the two sets are shown in Tables 10-11.

TABLE 10

Characteristics of NSCLC patients and cancer-free smokers in a training set

| | NSCLC cases (n = 64) | Controls (n = 32) | P-value |
|---|---|---|---|
| Age | 66.98 (SD 9.08) | 62.66 (SD 15.04) | 0.14 |
| Sex | | | 0.33 |
| Female | 16 | 8 | |
| Male | 48 | 24 | |
| Smoking pack-years (median) | 33.19 | 30.25 | 0.16 |
| Stage | | | |
| Stage I | 15 | | |
| Stage II | 9 | | |
| Stage III | 16 | | |
| Stage IV | 19 | | |
| Unknown | 5 | | |
| Histological type | | | |
| Adenocarcinoma | 32 | | |
| Squamous cell carcinoma | 32 | | |

Abbreviations: NSCLC, non-small cell lung cancer.

TABLE 11

Characteristics of NSCLC patients and cancer-free smokers in a testing set

| | NSCLC cases (n = 40) | Controls (n = 20) | P-value |
|---|---|---|---|
| Age | 67.38 (SD 9.17) | 62.66 (SD 13.54) | 0.23 |
| Sex | | | 0.46 |
| Female | 10 | 5 | |
| Male | 30 | 15 | |
| Smoking pack-years (median) | 32.64 | 29.28 | 0.23 |
| Stage | | | |
| Stage I | 10 | | |
| Stage II | 8 | | |
| Stage III | 12 | | |
| Stage IV | 10 | | |
| Histological type | | | |
| Adenocarcinoma | 22 | | |
| Squamous cell carcinoma | 18 | | |

Abbreviations: NSCLC, non-small cell lung cancer.

RNA Isolation and Quantitative Reverse Transcriptase PCR

RNA was extracted from the specimens by using Trizol L S reagent (Invitrogen Carlsbad, Calif.) and RNeasy Mini Kit (Qiagen, Hilden, Germany) (Ma J, Jemal A, Smith R: Reply to lung cancer deaths averted by screening should be considered in the context of tobacco control policies. Cancer 2013, 119(18):3420-3421; Shen J, Liu Z, Todd N W, Zhang H, Liao J, Yu L, Guarnera M A, Li R, Cai L, Zhan M et al: Diagnosis of lung cancer in individuals with solitary pulmonary nodules by plasma microRNA biomarkers. BMC Cancer 2011, 11:374; Shen J, Todd N W, Zhang H, Yu L, Lingxiao X, Mei Y, Guarnera M, Liao J, Chou A, Lu C L et al: Plasma microRNAs as potential biomarkers for non-small-cell lung cancer. Lab Invest 2011, 91(4):579-587). RT was carried out to generate cDNA by using a RT Kit (Applied Biosystems, Foster City, Calif.) as described in our published works (Ma J, Jemal A, Smith R: Reply to lung cancer deaths averted by screening should be considered in the context of tobacco control policies. Cancer 2013, 119 (18):3420-3421; Shen J, Liu Z, Todd N W, Zhang H, Liao J, Yu L, Guarnera M A, Li R, Cai L, Zhan M et al: Diagnosis of lung cancer in individuals with solitary pulmonary nodules by plasma microRNA biomarkers. BMC Cancer 2011, 11:374; Shen J, Todd N W, Zhang H, Yu L, Lingxiao X, Mei Y, Guarnera M, Liao J, Chou A, Lu C L et al: Plasma microRNAs as potential biomarkers for non-small-cell lung cancer. Lab Invest 2011, 91(4):579-587). PCR was performed to measure expressions of target genes by using a PCR kit (Applied Biosystems) on a Bio-Red IQ5 Muiltcolor RT-PCR Detection System (Bio-Red, Hercules, Calif.). Primers and probes of the targeted 13 FUTs genes are shown in the Supplementary Table 3. Expression levels of the genes were determined using comparative cycle threshold (Ct) method with the equation 2-$\Delta\Delta$Ct by using miR-1228 as an internal control (Shen J, Liu Z, Todd N W, Zhang H, Liao J, Yu L, Guarnera M A, Li R, Cai L, Zhan M et al: Diagnosis of lung cancer in individuals with solitary pulmonary nodules by plasma microRNA biomarkers. BMC Cancer 2011, 11:374; Shen J, Todd N W, Zhang H, Yu L, Lingxiao X, Mei Y, Guarnera M, Liao J, Chou A, Lu C L et al: Plasma microRNAs as potential biomarkers for non-small-cell lung cancer. Lab Invest 2011, 91(4):579-587; Lin Y, Leng Q, Jiang Z, Guarnera M A, Zhou Y, Chen X, Wang H, Zhou W, Cai L, Fang H et al: A classifier integrating plasma biomarkers and radiological characteristics for distinguishing malignant from benign pulmonary nodules. Int J Cancer 2017, 141(6):1240-1248; Ma J, Mannoor K, Gao L, Tan A, Guarnera M A, Zhan M, Shetty A, Stass S A, Xing L, Jiang F: Characterization of microRNA transcriptome in lung cancer by next-generation deep sequencing. Mol Oncol 2014, 8(7):1208-1219; Xing L, Todd N W, Yu L, Fang H, Jiang F: Early detection of squamous cell lung cancer in sputum by a panel of microRNA markers. Mod Pathol 2010, 23(8):1157-1164; Benz F, Roderburg C, Vargas Cardenas D, Vucur M, Gautheron J, Koch A, Zimmermann H, Janssen J, Nieuwenhuijsen L, Luedde M et al: U6 is unsuitable for normalization of serum miRNA levels in patients with sepsis or liver fibrosis. Exp Mol Med 2013, 45:e42). The targeted genes with Ct values>35 were considered to be below the detection level of qRT-PCR (Guthrie J L, Seah C, Brown S, Tang P, Jamieson F, Drews S J: Use of Bordetella pertussis BP3385 to establish a cutoff value for an IS481-targeted real-time PCR assay. J Clin Microbiol 2008, 46(11):3798-3799).

Droplet Digital PCR ddPCR for analysis of expression level of the genes was performed as described in our previous work (Li N, Ma J, Guarnera M A, Fang H, Cai L, Jiang F: Digital PCR quantification of miRNAs in sputum for diagnosis of lung cancer. J Cancer Res Clin Oncol 2014, 140(1):145-150; Ma J, Li N, Guarnera M, Jiang F: Quantification of Plasma miRNAs by Digital PCR for Cancer Diagnosis. Biomark Insights 2013, 8:127-136). Briefly, TaqMan™ reaction mix (Applied Biosystems) containing sample cDNA was partitioned into aqueous droplets in oil via the QX100 Droplet Generator (Bio-Rad), and then transferred to a 96-well PCR plate. A two-step thermocycling protocol (95° C.×10 min; 40 cycles of [94° C.×30 s, 60° C.×60 s], 98° C.×10 min) was undertaken in a Bio-Rad C1000 (Bio-Rad). The PCR plate was loaded on Droplet Reader (Bio-Rad), by which copy number of each gene per μl PCR reaction was directly determined. We used QuantaSoft 1.7.4 analysis software (Bio-Rad) and Poisson statistics to compute droplet concentrations (copies/μL). All assays were done in triplicates, and one no-template control and two interplate controls were carried along in each experiment.

Statistical Analysis

Pearson's correlation analysis was applied to assess relationship between gene expressions and demographic and clinical characteristics of the lung cancer patients and control individuals. The area under receiver operating characteristic (ROC) curve (AUC) analyses were used to determine sensitivity, specificity, and corresponding cut-off value of each gene (Dodd L E, Pepe M S: Partial AUC estimation and regression. Biometrics 2003, 59(3):614-623). All P values shown were two sided, and a P value of <0.05 was considered statistically significant.

Results

Figure 3:
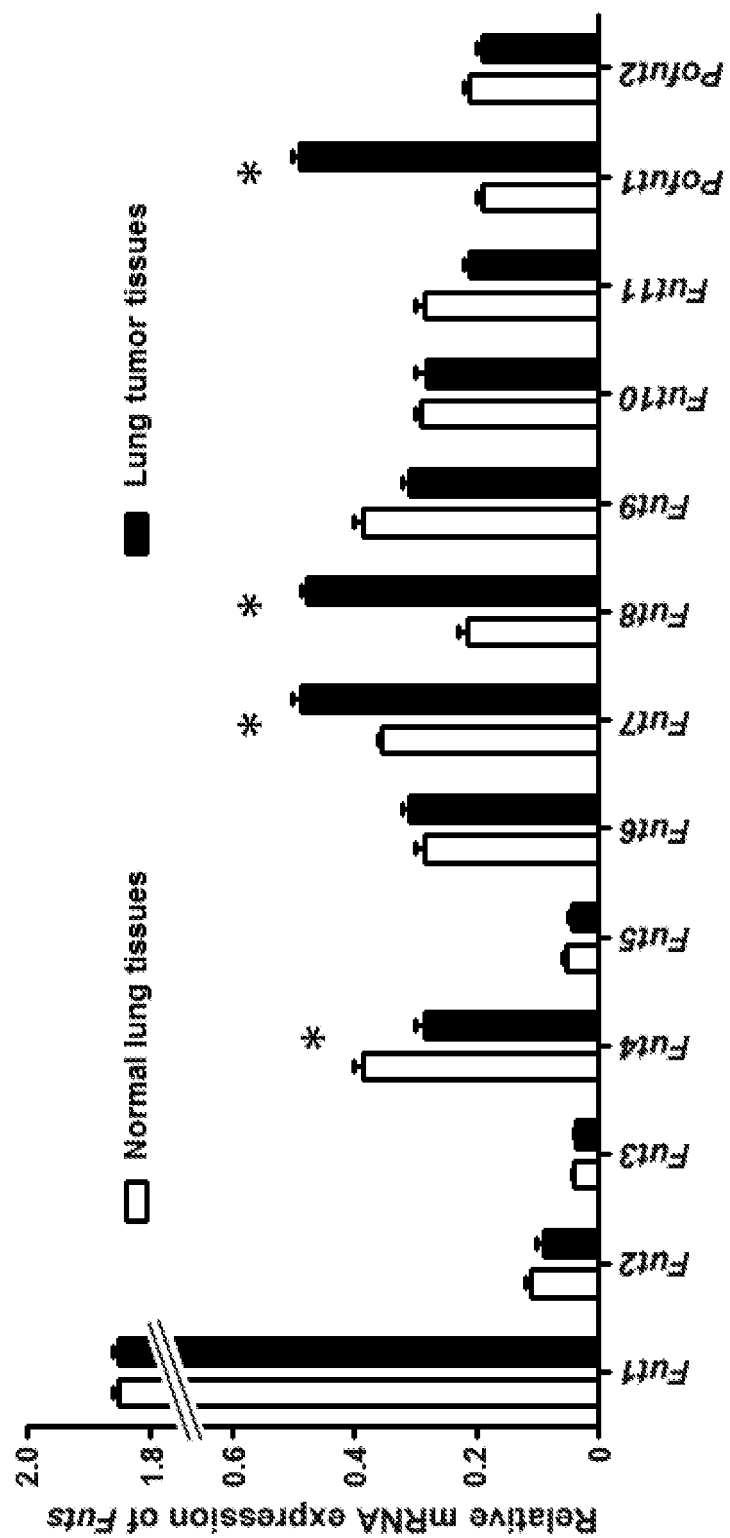
FIG. 3. mRNA expression levels of 13 Futs in surgical lung tumor tissues and the paired noncancerous lung tissues. Four genes (Futs-4, 7 and 8, and pofut1) show a different level in lung tumor tissues as compared with the paired noncancerous lung tissues (All p<0.05).

Identifying Futs Whose Abnormal Transcriptional Levels were Associated with Lung Cancer The transcription levels of all 13 Futs were examined by using qRT-PCR in 48 stage I NSCLC tissues and the matched noncancerous lung tissues. Three (Futs-7 and 8, and pofut1) displayed a higher, whereas one gen (Fut-4) exhibited a lower mRNA expression levels in lung cancer tissues compared with the matched noncancerous lung tissues (All p<0.05) (FIG. 3). There was no significant difference of the expression of the Futs between histological types of lung cancer (All p>0.05).

Developing a Panel of Plasma Fut Biomarkers for Lung Cancer Early Detection

We measured transcriptional levels of the 4 Futs in plasma by using qRT-PCR in a training set of 64 cases and 32 controls by qRT-PCR. Ct value of qPCR for the 4 Futs in the plasma samples was more than 35. The amplification curves of the RT-PCR analysis for the genes were not reliably generated. Therefore, the expression levels of the 4 lung tumor-associated Futs in plasma was too low to be detectable by qRT-PCR. We have previously demonstrated that ddPCR is a direct method for absolutely and quantitatively measuring nucleic acids. Furthermore, ddPCR does not require a reliance on rate-based measurements (CT values), endogenous controls, and calibration curves. In addition, ddPCR needs much less RNA compared with RT-PCR, and is particularly useful in the quantification of the genes that have endogenous low-level expression in plasma samples. We, therefore, used ddPCR to determine expression level of the 4 Futs in the plasma samples. Each well of the samples contained at least 10,000 droplets. By contrast, no product was synthesized in the negative control samples. Thus, the plasma samples were successfully "read" by ddPCR for the absolute quantification of the 4 Fut genes.

Figure 4:
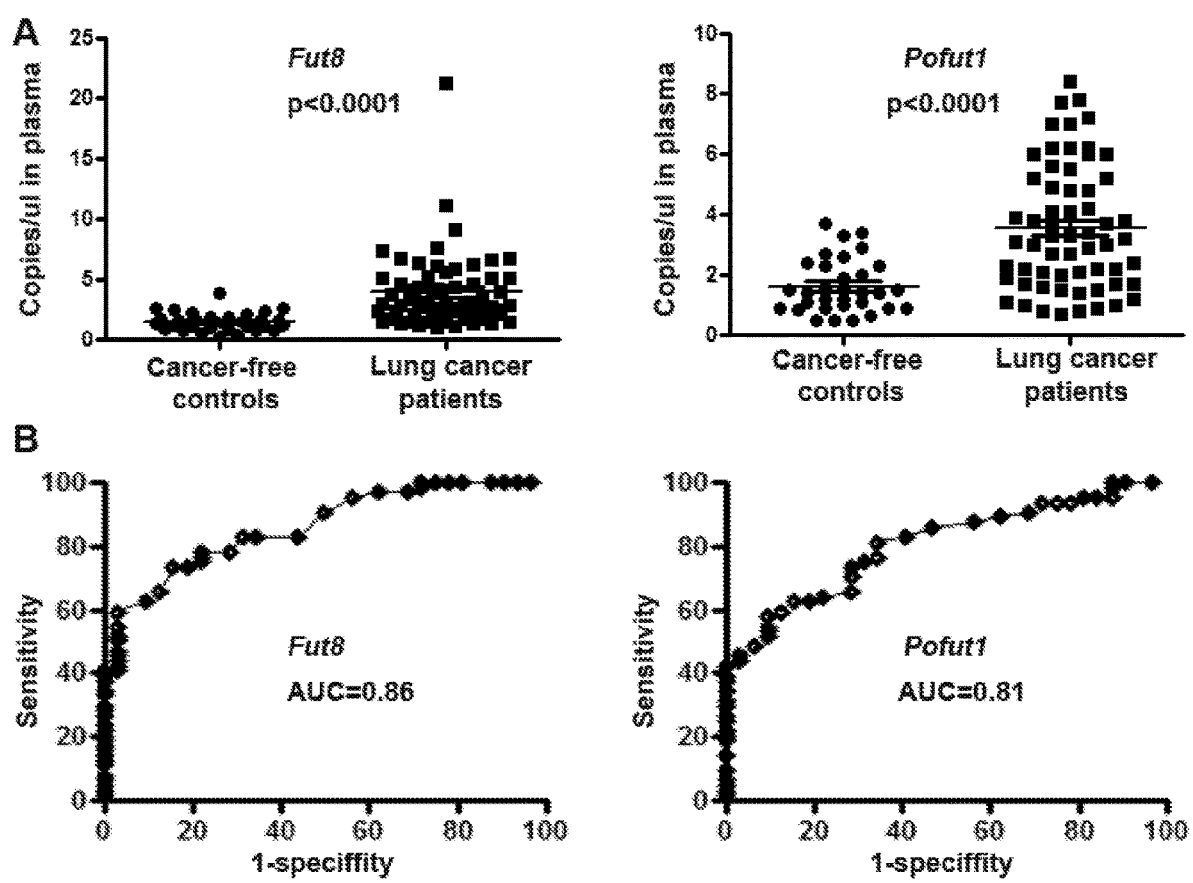
FIG. 4. mRNA expression levels of Fut8 and Pofut1 in plasma samples of 64 lung cancer patients and 32 cancer-free controls. (A), Fut8 and Pofut1 displayed a higher plasma level in lung cancer patients vs. cancer-free controls (all p<0.0001). (B), the receiver operating characteristic (ROC) curves of Fut8 and Pofut1 produced an area under the ROC curve (AUC) of 0.86 and 0.81, respectively, in diagnosis of lung cancer.
Figure 5:
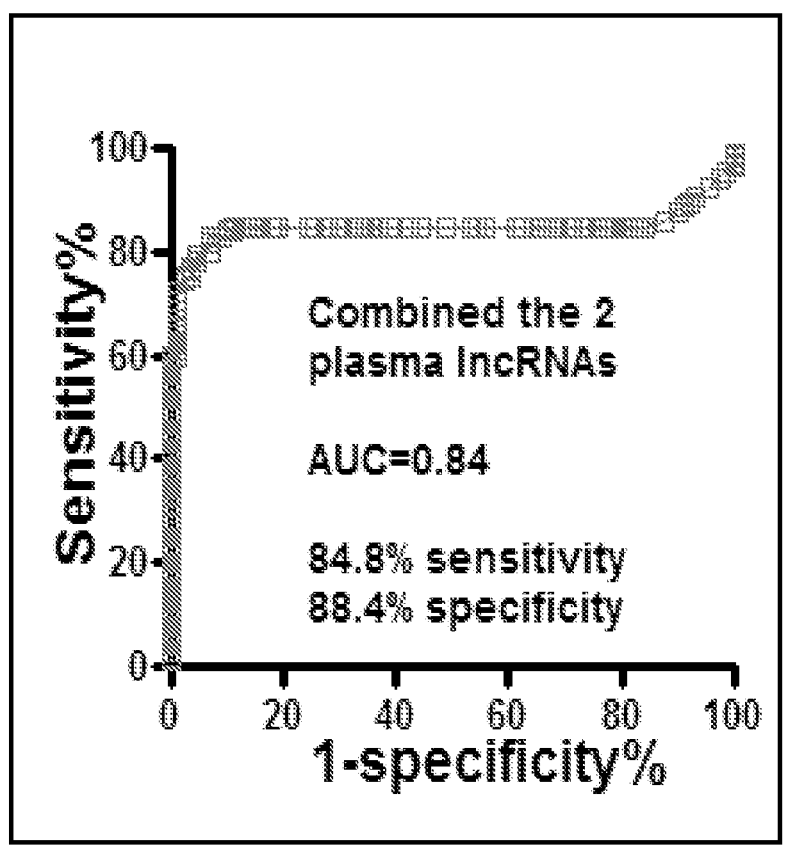
FIG. 5. Receiver-operator characteristic (ROC) curve analysis of the 2 combined plasma lncRNAs (SNHG1 and RMRP). The area under the ROC curve (AUC) conveys its accuracy for diagnosis of malignant PNs.

Of the 4 Futs, Fut8 and Pofut1 had a high expression level in plasma of lung cancer patients vs. cancer-free controls (All P<0.05) (FIG. 4A). Pearson's correlation analysis showed that there were significant correlations between the expression levels of the 2 genes in plasma and those in the surgical tissue specimens (All r≥0.92, all P≤0.05). Therefore, the level of Fut8 and Pofut1 in plasma might reflect those in the tumors of the lung cancer patients. However, other 2 genes (Fut4 and Fut8) did not display a different plasma expression in lung cancer cases vs. controls. Furthermore, Fut8 and Pofut1 exhibited AUC values of 0.86 and 0.81, respectively, in distinguishing NSCLC patients from the healthy individuals (FIG. 4B). Using Youden's index (Schisterman E F, Perkins N J, Liu A, Bondell H: Optimal cut-point and its corresponding Youden Index to discriminate individuals using pooled blood samples. Epidemiology 2005, 16(1):73-81)[32], we set up optimal cutoff for the two FUTs at 1.56 and 1.64, respectively. As a result, the use of the individual genes alone produced 62.50-73.44% sensitivities and 90.63-90.88% specificities (Table 12).

TABLE 12

Diagnostic performance of one-gene and vs. combined use of the 2 genes for lung cancer diagnosis in a training set.

| | Accuracy | Sensitivity (95% CI) | Specificity (95% CI) |
|---|---|---|---|
| Fut8 | 79.17 (69.67 to 86.79) | 73.44 (60.20 to 83.56) | 90.88 (75.38 to 97.56) |
| Pofut1 | 71.88 (61.78 to 80.58) | 62.50 (49.87 to 79.29) | 90.63 (75.39 to 97.22) |
| Combined use of the 2 genes | 83.33 (74.33 to 91.16) | 81.76 (77.46 to 90.23) | 86.26 (79.20 to 92.49) |

Abbreviations: CI, confidence interval.

Combined use of the two genes based on at least one positive result in either Fut8 or Pofut1 produced the highest classification accuracy (0.833) compared to any one used alone (all p<0.05) (Table 12). The 2 genes used in combination created a sensitivity of 81.76% and a specificity of 86.26% for diagnosis of lung cancer, thus significantly improving the cancer detection rate by a single gene with only a 4% decrease in specificity (Table 12). Furthermore, the estimated correlation determined by Pearson correlation analysis among levels of the 2 genes was very low (r=0.187, p=0.06), further supporting that the combined analysis of the 2 FUT genes outperformed a single one for diagnosis of NSCLC. In addition, combined analysis of the 2 plasma biomarkers did not show special association with stage and histological type of lung cancer, and patients' age, gender, and smoking status (All P>0.05).

Validating the Sputum Markers in an Independent Set of Lung Cancer Patients and Controls To evaluate the diagnostic performance of the plasma biomarker panel, the 2 genes (Fut8 and Pofut1) were assessed in plasma samples of 40 NSCLC patients and 20 healthy controls. The 2 genes used in combination could differentiate the NSCLC patients from healthy controls with 82.50% sensitivity and 85.00% specificity. Furthermore, no statistically significant difference was found in the sensitivity and specificity of the markers for stages and histological types of NSCLC (All p>0.05). Moreover, there was no association of expressions of the 2 genes with the age, gender, or smoking status of the lung cancer patients and normal individuals (All p>0.05). Taken together, the results confirm that the panel of 2 plasma biomarkers could be used for the early detection of lung cancer.

Example 4. Increased Sensitivity and Specificity Signature of 3-Integromic Plasma Markers Lung cancer is a heterogeneous disease and develops from a multitude of molecular changes. miRNAs, lncRNAs, and glycosylation genes have diverse functions in carcinogenesis via different biological mechanisms. Using plasma of 66 lung cancer patients and 38 controls, we investigate if integrating the different biomarker types could have a synergistic effect.

We recently identified a panel of 2 plasma long non-coding RNAs (lncRNAs) biomarkers for lung cancer. Long non-coding RNAs (lncRNAs) (>200 bp) play critical and diverse regulatory roles in lung tumorigenesis through different molecular mechanisms from those of miRNAs. In plasma samples of 32 cancer-free subjects and 64 lung cancer patients, we used ddPCR to evaluate the 36 lncRNAs of lung tumors that were characterized by our NGS analysis (FIG. 8).

Figure 6:
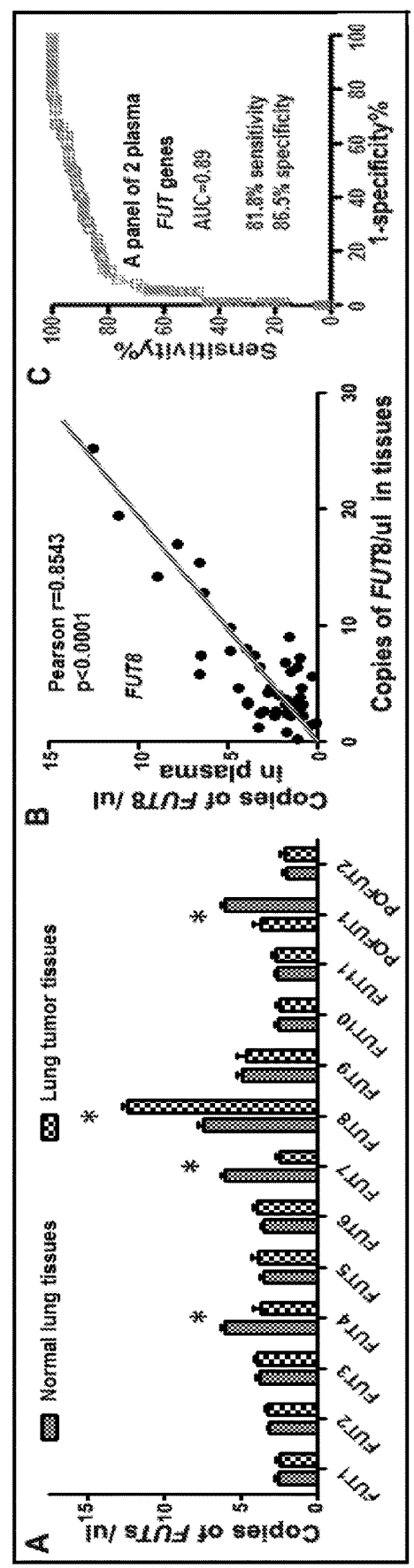
FIG. 6. Identification of a panel of 2 glycosylation genes as novel plasma biomarkers for lung cancer. (A) Copies of FUTs/µL for 13 FUTs comparing normal lung tissues and lung tumor tissues. (B) Comparison of FUT8 in plasma with tissues. (C) Receiver-operator characteristic (ROC) curve analysis of 2 plasma FUT genes (FUT8 and Pofut1). The area under the ROC curve (AUC) conveys its accuracy for diagnosis of malignant PNs.

We identified fucosylation genes as novel plasma biomarkers for lung cancer. Dysregulation of fucosylation plays an important role in lung carcinogenesis. We used ddPCR to measure RNA expression of all 13 FUT genes in plasma of 60 lung cancer patients and 30 cancer-free smokers, FUT8 and POFUT1 had a high expression level in lung cancer cases vs. controls. We identified a panel of 2 glycosylation genes as novel plasma biomarkers for lung cancer (FIG. 6).

Figure 7:
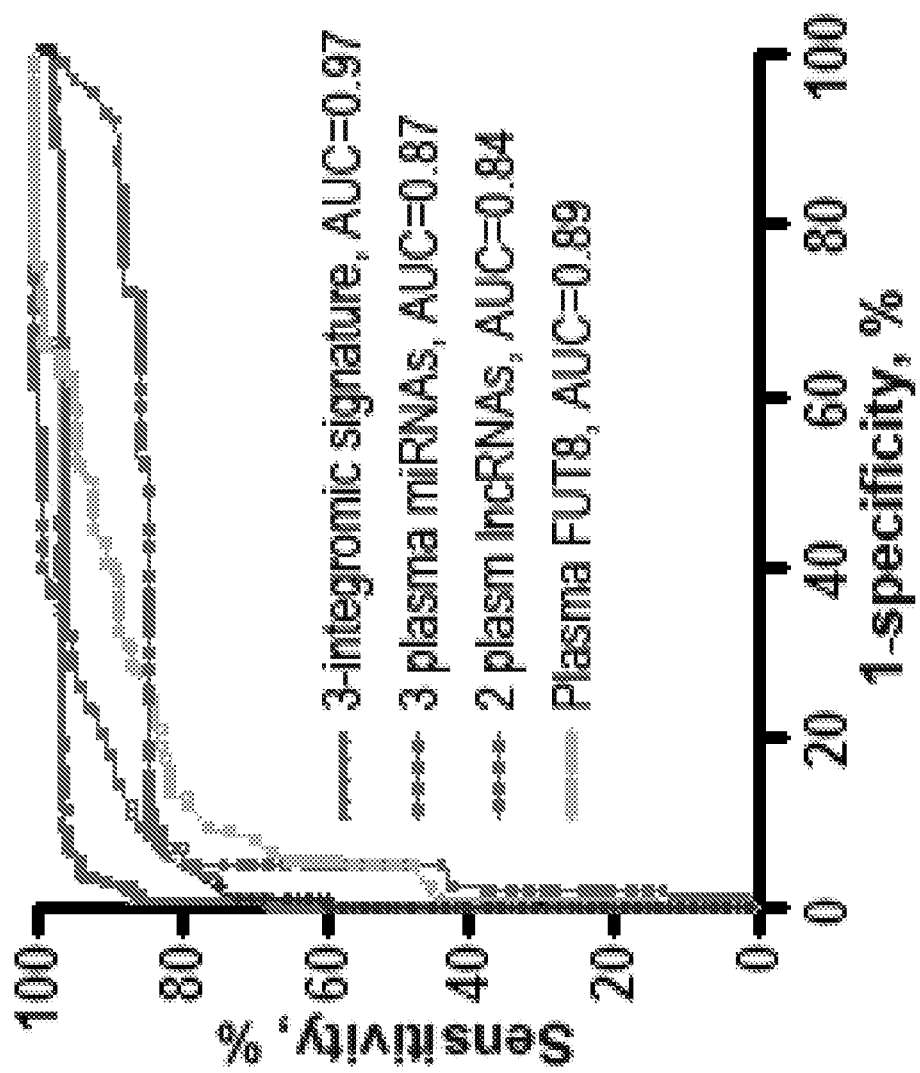
FIG. 7. Receiver-operator characteristic (ROC) curve analysis of the 3-integromic plasma markers (SNHG1, FUT8, and miR-210). The area under the ROC curve (AUC) conveys its accuracy for diagnosis of malignant PNs. From the marker panels, 3 genes were selected as a 3-integromic plasma marker signature: Probability of a lung cancer patient=−7.29+2.8*log (SNHG1)+3.83*log (FUT8)+3.36*log (miR-210).

From the marker panels, 3 genes were selected as a 3-integromic plasma marker signature. The probability of a lung cancer patient was calculated using: p=−7.29+2.8*log (SNHG1)+3.83*log (FUT8)+3.36*log (miR-210). The 3-integromic plasma marker signature had a greater AUC (0.97) with higher sensitivity (94.8%) and specificity (95.6%) than did the single type of biomarker (Table 13, FIG. 7). The performance is independent of stage and histology of lung cancer, and patients' age, sex, and ethnicity.

TABLE 13

Performances of the 3-integromic plasma signature and 3 different panels of biomarkers

| Biomarkers | Sensitivity (95% CI) | Specificity (95% CI) |
|---|---|---|
| 3-integromic signature | 94.8% (91.3% to 99.7%) | 95.6% (89.0% to 99.9%) |
| 3 plasma miRNAs | 81.2% (75.7% to 93.7%) | 86.2% (80.4% to 94.9%) |
| 2 plasma lncRNAs | 84.8% (77.7% to 93.7%) | 88.4% (80.4% to 94.9%) |
| 2 plasma FUTs | 81.8% (74.6% to 87.6%) | 86.5% (79.3% to 91.9%) |

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

What is claimed is:

1. A method for efficiently targeting the treatment of non-small cell lung cancer in a subject exhibiting a pulmonary nodule, the method comprising
   a. performing an assay that measures an expression level of miR205-5p in a plasma sample from the subject;
   b. performing an assay that measures an expression level of miR126 in a plasma sample from the subject;
   c. performing an assay that provides a size of the pulmonary nodule in the subject;
   d. calculating a probability value based on the combination of the expression levels of miR205-5p and miR126, and the size of the pulmonary nodule;
   e. if the probability value is below a specified threshold, considering the pulmonary nodule to be benign and so notifying the subject; and
   f. if the probability meets or exceeds the specified threshold, administering a treatment for non-small cell lung cancer to the subject, wherein the treatment is selected from administration of a therapeutic agent, surgery, radiofrequency ablation, radiation, and combinations thereof.

2. The method of claim 1, wherein calculating the probability of lung cancer comprises generating a receiver operating characteristic (ROC) curve; and
   calculating an area under the ROC curve (AUC), said area under the curve (AUC) providing the probability of lung cancer in the subject.

3. The method of claim 1, wherein the expression level of miR205-5p and/or miR126 is detected by quantitative RT-PCR.

4. The method of claim 1, wherein the expression level of the miR205-5p and/or miR126 is determined without the need of an internal control gene.

5. The method of claim 1, wherein the expression level of miR205-5p and/or miR126 is detected by droplet digital PCR.

6. The method of claim 1, wherein the subject is a current smoker.

7. The method of claim 1, wherein the subject is a former smoker.

8. The method of claim 1, wherein the subject has a smoking history selected from the group consisting of at least 15 pack-years, at least 20 pack-years, at least 25 pack-years at least 30 pack-years, at least 35 pack-years, at least 40 pack-years, at least 45 pack-years, at least 50 pack-years, at least 55 pack-years, at least 60 pack-years, and at least 65 pack-years.

9. The method of claim 1, wherein the subject is between 55 and 80 years old.

10. The method of claim 1, wherein the method further comprises assaying the plasma sample for contaminating miRNA.

11. The method of claim 10, wherein the contaminating miRNA is selected from the group consisting of RBC-related miRNA (mir-451), myeloid-related miRNA (miR-223), lymphoid-associated miRNA (miR-150) and combinations thereof.

12. The method of claim 1, wherein the pulmonary nodule that is non-small cell lung cancer is an adenocarcinoma, squamous cell carcinoma or large cell carcinoma.

13. The method of claim 1, wherein miR126 comprises SEQ ID NO:1.

14. The method of claim 1, wherein miR205-5p comprises SEQ ID NO:2.

15. The method of claim 1, wherein the probability value is calculated by a classifier having the following formula:

probability value=8687+1.5172×log(copy number of miR205-5p/µl plasma sample)−2.5117×log(copy number of miR-126/µl plasma sample)+0.8262× diameter of pulmonary nodule in centimeters.

* * * * *